(12) United States Patent
Gross

(10) Patent No.: US 11,065,451 B1
(45) Date of Patent: Jul. 20, 2021

(54) PROSTHETIC AORTIC VALVE PACING SYSTEMS

(71) Applicant: E-VALVE SYSTEMS LTD., Herzliya (IL)

(72) Inventor: Yossi Gross, Moshav Mazor (IL)

(73) Assignee: E-VALVE SYSTEMS LTD., Herzliya (IL)

( * ) Notice: Subject to any disclaimer, the term of this patent is extended or adjusted under 35 U.S.C. 154(b) by 0 days.

(21) Appl. No.: 17/142,729

(22) Filed: Jan. 6, 2021

(51) Int. Cl.

| | |
|---|---|
| A61N 1/362 | (2006.01) |
| A61N 1/05 | (2006.01) |
| A61N 1/378 | (2006.01) |
| A61N 1/372 | (2006.01) |
| A61N 1/365 | (2006.01) |
| A61F 2/24 | (2006.01) |
| A61B 5/28 | (2021.01) |

(52) U.S. Cl.
CPC .......... *A61N 1/3629* (2017.08); *A61F 2/2418* (2013.01); *A61N 1/057* (2013.01); *A61N 1/36507* (2013.01); *A61N 1/3787* (2013.01); *A61N 1/37229* (2013.01); *A61B 5/28* (2021.01); *A61F 2230/0065* (2013.01)

(58) Field of Classification Search
None
See application file for complete search history.

(56) References Cited

U.S. PATENT DOCUMENTS

| | | |
|---|---|---|
| 4,256,094 A | 3/1981 | Kapp et al. |
| 4,979,955 A | 12/1990 | Smith |
| 5,487,760 A | 1/1996 | Villafana |
| 6,030,335 A | 2/2000 | Franchi |
| 6,030,336 A | 2/2000 | Franchi |
| 6,050,932 A | 4/2000 | Franchi |

(Continued)

FOREIGN PATENT DOCUMENTS

| | | |
|---|---|---|
| EP | 3508113 | 7/2019 |
| FR | 3034650 | 10/2016 |

(Continued)

OTHER PUBLICATIONS

"Pacing at the Bundle of His," Medtronic, Inc., Minneapolis, MN, USA (Oct. 2017).

(Continued)

*Primary Examiner* — Brian T Gedeon
(74) *Attorney, Agent, or Firm* — Sughrue Mion, PLLC

(57) ABSTRACT

A prosthetic aortic valve is configured to be delivered to a native aortic valve of a patient in a constrained delivery configuration within a delivery sheath. The prosthetic aortic valve includes a frame; a plurality of prosthetic leaflets coupled to the frame; a cathode and an anode, which are mechanically coupled to the frame; and a prosthetic-valve coil, which is coupled to the frame and is in non-wireless electrical communication with the cathode and the anode. When the prosthetic aortic valve is in an expanded fully-deployed configuration upon release from the delivery sheath, (a) a line defined between upstream-most and downstream-most points of mechanical coupling between the prosthetic-valve coil and the frame and (b) a central longitudinal axis defined by the frame form an angle of between 20 and 70 degrees. Other embodiments are also described.

27 Claims, 13 Drawing Sheets

(56) References Cited

U.S. PATENT DOCUMENTS

| | | | |
|---|---|---|---|
| 7,643,879 B2 | 1/2010 | Shuros et al. | |
| 7,914,569 B2 | 3/2011 | Nguyen et al. | |
| 8,092,365 B2 | 1/2012 | Rinderknecht et al. | |
| 8,239,023 B2 | 8/2012 | Shuros et al. | |
| 9,005,106 B2 | 4/2015 | Gross et al. | |
| 9,326,854 B2 | 5/2016 | Casley et al. | |
| 9,526,637 B2* | 12/2016 | Dagan | A61B 5/0816 |
| 9,662,211 B2 | 5/2017 | Hodson et al. | |
| 9,737,264 B2 | 8/2017 | Braido et al. | |
| 9,808,201 B2* | 11/2017 | Braido | A61B 17/0057 |
| 10,543,083 B2* | 1/2020 | Gross | A61F 2/24 |
| 10,758,725 B2 | 9/2020 | Daniels et al. | |
| 10,835,750 B2 | 11/2020 | Gross | |
| 2003/0032853 A1 | 2/2003 | Korakianitis et al. | |
| 2004/0024285 A1 | 2/2004 | Muckier | |
| 2004/0097784 A1 | 5/2004 | Peters et al. | |
| 2004/0111006 A1 | 6/2004 | Alfemess et al. | |
| 2005/0049696 A1 | 3/2005 | Siess et al. | |
| 2008/0077016 A1 | 3/2008 | Sparks et al. | |
| 2010/0197994 A1* | 8/2010 | Mehmanesh | A61M 60/135 600/18 |
| 2011/0071351 A1 | 3/2011 | Sperling | |
| 2011/0137370 A1 | 6/2011 | Gross et al. | |
| 2011/0196482 A1* | 8/2011 | Forsell | A61F 2/2403 623/2.17 |
| 2012/0245678 A1 | 9/2012 | Solem | |
| 2012/0265296 A1 | 10/2012 | McNamara et al. | |
| 2012/0296382 A1 | 11/2012 | Shuros et al. | |
| 2013/0138205 A1 | 5/2013 | Kushwaha et al. | |
| 2013/0297009 A1 | 11/2013 | Chalekian et al. | |
| 2014/0066895 A1 | 3/2014 | Kipperman | |
| 2014/0081154 A1* | 3/2014 | Toth | A61B 5/0261 600/479 |
| 2014/0180391 A1 | 6/2014 | Dagan et al. | |
| 2014/0275720 A1 | 9/2014 | Ferrari | |
| 2015/0128684 A1 | 5/2015 | Hodson et al. | |
| 2016/0045165 A1 | 2/2016 | Braido et al. | |
| 2016/0045316 A1* | 2/2016 | Braido | A61B 5/026 623/2.38 |
| 2016/0144091 A1 | 5/2016 | Breedon et al. | |
| 2016/0278951 A1 | 9/2016 | Dagan et al. | |
| 2017/0100527 A1 | 4/2017 | Schwammenthal et al. | |
| 2017/0258585 A1 | 9/2017 | Marquez et al. | |
| 2017/0266433 A1 | 9/2017 | Daniels et al. | |
| 2019/0076588 A1 | 3/2019 | Ochsner et al. | |
| 2019/0209302 A1 | 7/2019 | Gross | |
| 2020/0139121 A1 | 5/2020 | Gross | |
| 2020/0261224 A1 | 8/2020 | Gross | |
| 2020/0282204 A1 | 9/2020 | Capek et al. | |

FOREIGN PATENT DOCUMENTS

| | | |
|---|---|---|
| WO | 2013/035092 | 3/2013 |
| WO | 2014/043235 | 3/2014 |
| WO | 2016/157183 | 10/2016 |

OTHER PUBLICATIONS

"Medtronic Evolut™ PRO System brochure," Medtronic, Inc., Minneapolis, MN, USA (Mar. 2017).

"Medtronic CoreValve™ System Instructions for Use," Medtronic, Inc., Minneapolis, MN, USA (2014).

An Office Action dated Apr. 11, 2019, which issued during the prosecution of U.S. Appl. No. 15/864,661.

European Search Report dated May 17, 2019 which issued during the prosecution of Applicant's European App No. 19150581.7.

Jobanputra Y et al., "Rapid Ventricular Pacing During Transcatheter Valve Procedures Using an Internal Device and Programmer: A Demonstration of Feasibility," JACC Mar. 20, 2018, vol. 71, Issue 11, p. 1381.

An Office Action dated Apr. 27, 2020, which issued during the prosecution of U.S. Appl. No. 16/734,798.

Notice of Allowance dated Aug. 3, 2020, which issued during the prosecution of U.S. Appl. No. 16/734,798.

Notice of Allowance dated Jan. 25, 2021, which issued during the prosecution of U.S. Appl. No. 16/868,121.

An Office Action dated Nov. 23, 2020, which issued during the prosecution of U.S. Appl. No. 16/868,121.

Notice of Allowance dated Sep. 26, 2019, which issued during the prosecution of U.S. Appl. No. 15/864,661.

* cited by examiner

PROSTHETIC AORTIC VALVE PACING SYSTEMS

FIELD OF THE APPLICATION

The present invention relates generally to surgical systems, and specifically to pacing systems.

BACKGROUND OF THE APPLICATION

Aortic heart valve replacement may be necessary to treat valve regurgitation or stenotic calcification of the leaflets. In percutaneous transluminal delivery techniques, a prosthetic aortic valve is compressed for delivery in a catheter and advanced through the descending aorta to the heart, where the prosthetic valve is deployed in the aortic valve annulus. New-onset cardiac conduction disturbances are common after transcatheter aortic valve implantation (TAVI). The most common complication is left bundle branch block (LBBB).

US Patent Application Publication 2019/0209302 to Gross, which is incorporated herein by reference, describes a method of assembling an electronic prosthetic aortic valve, the method including inserting an electronics component into a valve component, the electronics component including one or more electrodes and a prosthetic-valve coil, and the valve component including a frame and prosthetic leaflets coupled to the frame; and coupling the electronics component to the valve component.

US Patent Application Publication 2020/0139121 to Gross, which is incorporated herein by reference, describes a valve prosthesis system, which includes a prosthetic aortic valve and a non-implantable unit. The prosthetic aortic valve includes a plurality of prosthetic leaflets; a frame; a cathode and an anode, which are mechanically coupled to the frame; and a prosthetic-valve coil, which is in non-wireless electrical communication with the cathode and the anode. The non-implantable unit includes an energy-transmission coil; and non-implantable control circuitry, which is configured to drive the cathode and the anode to apply a pacing signal and to set parameters of the pacing signal, by wirelessly transferring energy from the energy-transmission coil to the prosthetic-valve coil by inductive coupling.

US Patent Application Publication 2020/0261224 to Gross, which is incorporated herein by reference, describes a valve prosthesis system that includes a prosthetic aortic valve and a non-implantable unit. The prosthetic aortic valve includes a plurality of prosthetic leaflets; a frame; a cathode and an anode, which are mechanically coupled to the frame; and a prosthetic-valve coil, which is in non-wireless electrical communication with the cathode and the anode. The prosthetic aortic valve does not include any active electronic components. The non-implantable unit includes an energy-transmission coil; sensing skin ECG electrodes; and non-implantable control circuitry, which drives the cathode and the anode to apply a pacing signal to a heart, detect at least one cardiac parameter using the sensing skin ECG electrodes, and, at least partially responsively to the detected cardiac parameter, to set parameters of the pacing signal, by wirelessly transferring energy from the energy-transmission coil to the prosthetic-valve coil by inductive coupling.

U.S. Pat. No. 7,914,569 to Nguyen et al., which is incorporated herein by reference, describes a heart valve prosthesis having a self-expanding multi-level frame that supports a valve body comprising a skirt and plurality of coapting leaflets. The frame transitions between a contracted delivery configuration that enables percutaneous transluminal delivery, and an expanded deployed configuration having an asymmetric hourglass shape. The valve body skirt and leaflets are constructed so that the center of coaptation may be selected to reduce horizontal forces applied to the commissures of the valve, and to efficiently distribute and transmit forces along the leaflets and to the frame. Alternatively, the valve body may be used as a surgically implantable replacement valve prosthesis.

SUMMARY OF THE APPLICATION

Some embodiments of the present invention provide a prosthetic aortic valve, which is configured to be delivered to a native aortic valve of a patient in a constrained delivery configuration within a delivery sheath. The prosthetic aortic valve comprises a frame; a plurality of prosthetic leaflets coupled to the frame; a cathode and an anode, which are mechanically coupled to the frame; and a prosthetic-valve coil, which is coupled to the frame and is in non-wireless electrical communication with the cathode and the anode. When the prosthetic aortic valve is in an expanded fully-deployed configuration upon release from the delivery sheath, (a) a line defined between upstream-most and downstream-most points of mechanical coupling between the prosthetic-valve coil and the frame and (b) a central longitudinal axis defined by the frame form an angle of between 20 and 70 degrees, such as between 30 and 60 degrees, e.g., between 40 and 50 degrees, such as 45 degrees.

For some applications, a valve prosthesis system is provided that comprises the prosthetic aortic valve and an external unit. The external unit is configured to be disposed outside a body of the patient and comprises (a) an energy-transmission coil, and (b) external-unit control circuitry, which is configured to drive the energy-transmission coil to wirelessly transfer energy, by inductive coupling, to the prosthetic-valve coil when the prosthetic aortic valve is in the expanded fully-deployed configuration.

For some of these applications, the energy-transmission coil is configured to be positioned against the patient's chest, typically over a sternum. This positioning of the energy-transmission coil provides high transmission efficiency, because the respective axes of the energy-transmission coil and the prosthetic-valve coil are generally aligned, because of the angle formed between the prosthetic-valve coil and the central longitudinal axis of the frame described hereinabove. This high transmission efficiency may allow the prosthetic-valve coil and/or the energy-transmission coil to include fewer turns of the coil(s) and/or to have smaller diameters. Alternatively or additionally, this high transmission efficiency may allow the external unit to use less power to induce the same amount of current in the prosthetic-valve coil.

For other applications, the energy-transmission coil is configured to be positioned around the patient's neck. This positioning of the energy-transmission coil provides high transmission efficiency, because the respective axes of the energy-transmission coil and the prosthetic-valve coil are generally aligned, because of the angle formed between the prosthetic-valve coil and the central longitudinal axis of the frame described hereinabove.

For some applications, when the prosthetic aortic valve is in the expanded fully-deployed configuration, (a) the downstream-most point of mechanical coupling between the prosthetic-valve coil and the frame and (b) a centroid of the cathode are rotationally aligned with each other or rotationally offset from each other about the central longitudinal axis of the frame by less than 50 degrees, such as less than 30 degrees. Because of this rotational alignment, aligning the cathode adjacent to cardiac tissue near the bundle of His (facing generally posteriorly) automatically aligns the prosthetic-valve coil facing generally in the opposite direction, facing generally anterio-superiorly toward the sternum. This orientation provides good wireless coupling with the energy-transmission coil.

There is therefore provided, in accordance with an Inventive Concept 1 of the present invention, a prosthetic aortic valve, which is configured to be delivered to a native aortic valve of a patient in a constrained delivery configuration within a delivery sheath, and which includes:
 a frame;
 a plurality of prosthetic leaflets coupled to the frame;
 a cathode and an anode, which are mechanically coupled to the frame; and
 a prosthetic-valve coil, which is coupled to the frame and is in non-wireless electrical communication with the cathode and the anode,
 wherein when the prosthetic aortic valve is in an expanded fully-deployed configuration upon release from the delivery sheath, (a) a line defined between upstream-most and downstream-most points of mechanical coupling between the prosthetic-valve coil and the frame and (b) a central longitudinal axis defined by the frame form an angle of between 20 and 70 degrees.

Inventive Concept 2. The prosthetic aortic valve according to Inventive Concept 1, wherein the angle is between 30 and 60 degrees.

Inventive Concept 3. The prosthetic aortic valve according to Inventive Concept 1, wherein respective non-electrically-insulated end portions of the prosthetic-valve coil define the cathode and the anode.

Inventive Concept 4. The prosthetic aortic valve according to Inventive Concept 1, wherein the prosthetic aortic valve does not include any active electronic components.

Inventive Concept 5. The prosthetic aortic valve according to Inventive Concept 1, wherein when the prosthetic aortic valve is in the expanded fully-deployed configuration, the central longitudinal axis passes through a space surrounded by the prosthetic-valve coil.

Inventive Concept 6. The prosthetic aortic valve according to Inventive Concept 1, wherein when the prosthetic aortic valve is in the expanded fully-deployed configuration, (a) a downstream-most point of mechanical coupling between the prosthetic-valve coil and the frame and (b) a centroid of the cathode are rotationally aligned with each other or rotationally offset from each other about the central longitudinal axis by less than 50 degrees.

Inventive Concept 7. The prosthetic aortic valve according to Inventive Concept 1, wherein the cathode is located upstream of the anode along the frame.

Inventive Concept 8. The prosthetic aortic valve according to any one of Inventive Concepts 1-7,
 wherein when the prosthetic aortic valve is in the expanded fully-deployed configuration, the frame is shaped so as to define:
  (a) an upstream inflow portion,
  (b) a downstream outflow portion, and
  (c) a constriction portion, which is axially between the upstream inflow portion and the downstream outflow portion, wherein the prosthetic leaflets are coupled to the constriction portion, and wherein when the prosthetic aortic valve is in the expanded fully-deployed configuration, free edges of the prosthetic leaflets face toward the downstream outflow portion, and
 wherein the cathode is coupled to the upstream inflow portion of the frame.

Inventive Concept 9. The prosthetic aortic valve according to any one of Inventive Concepts 1-7,
 wherein when the prosthetic aortic valve is in the expanded fully-deployed configuration, the frame is shaped so as to define:
  (a) an upstream inflow portion,
  (b) a downstream outflow portion, and
  (c) a constriction portion, which is axially between the upstream inflow portion and the downstream outflow portion, wherein the prosthetic leaflets are coupled to the constriction portion, and wherein when the prosthetic aortic valve is in the expanded fully-deployed configuration, (A) free edges of the prosthetic leaflets face toward the downstream outflow portion, and (B) a ring-shaped longitudinal border between the downstream outflow portion and the constriction portion is defined by a downstream-most point of the frame to which the prosthetic leaflets are coupled, and
 wherein a downstream-most point of mechanical coupling between the prosthetic-valve coil and the frame is located on the downstream outflow portion when the prosthetic aortic valve is in the expanded fully-deployed configuration.

Inventive Concept 10. The apparatus according to Inventive Concept 9, wherein an upstream-most point of mechanical coupling between the prosthetic-valve coil and the frame is located on the constriction portion when the prosthetic aortic valve is in the expanded fully-deployed configuration.

Inventive Concept 11. A valve prosthesis system including the prosthetic aortic valve according to any one of Inventive Concepts 1-7, the valve prosthesis system further including an external unit, which is configured to be disposed outside a body of the patient, and which includes:
 an energy-transmission coil; and
 external-unit control circuitry, which is configured to drive the energy-transmission coil to wirelessly transfer energy to the prosthetic-valve coil by inductive coupling.

Inventive Concept 12. The valve prosthesis system according to Inventive Concept 11, wherein the external-unit control circuitry is configured to drive the cathode and the anode to apply a pacing signal to a heart of the patient, by wirelessly transferring the energy from the energy-transmission coil to the prosthetic-valve coil by inductive coupling.

Inventive Concept 13. The valve prosthesis system according to Inventive Concept 12,
 wherein the external unit further includes a cardiac sensor, and
 wherein the external-unit control circuitry is configured to:
  detect at least one cardiac parameter using the cardiac sensor, and
  at least partially responsively to the detected at least one cardiac parameter, set parameters of the pacing signal, by wirelessly transferring the energy from the energy-transmission coil to the prosthetic-valve coil by inductive coupling.

Inventive Concept 14. The valve prosthesis system according to Inventive Concept 13, wherein the cardiac sensor includes at least two sensing skin ECG electrodes.

Inventive Concept 15. The valve prosthesis system according to Inventive Concept 11,
 wherein the external-unit control circuitry is configured to wirelessly transfer the energy by generating a plurality of AC pulses, each including a train of AC bursts, and wherein the prosthetic aortic valve includes a passive diode, which is coupled in electrical communication with the prosthetic-valve coil, and is configured to rectify current in the prosthetic-valve coil.

Inventive Concept 16. The valve prosthesis system according to Inventive Concept 15, wherein the external-unit control circuitry is configured to generate the train of AC bursts at a frequency of between 3 kHz and 130 kHz.

Inventive Concept 17. The valve prosthesis system according to Inventive Concept 15, wherein the external-unit control circuitry is configured to include 20-100 AC bursts in each of the AC pulses.

There is further provided, in accordance with an Inventive Concept 18 of the present invention, a method including:

delivering, to a native aortic valve of a patient, via vasculature of the patient, a prosthetic aortic valve while in a constrained delivery configuration within a delivery sheath, the prosthetic aortic valve including (a) a frame, (b) a plurality of prosthetic leaflets coupled to the frame, (c) a cathode and an anode, which are mechanically coupled to the frame, and (d) a prosthetic-valve coil, which is coupled to the frame in non-wireless electrical communication with the cathode and the anode; and releasing the prosthetic aortic valve from the delivery sheath, such that the prosthetic aortic valve transitions to an expanded fully-deployed configuration, in which (a) a line defined between upstream-most and downstream-most points of mechanical coupling between the prosthetic-valve coil and the frame and (b) a central longitudinal axis defined by the frame form an angle of between 20 and 70 degrees.

Inventive Concept 19. The method according to Inventive Concept 18, wherein the angle is between 30 and 60 degrees.

Inventive Concept 20. The method according to Inventive Concept 18, wherein the prosthetic aortic valve does not include any active electronic components.

Inventive Concept 21. The method according to Inventive Concept 18, wherein releasing the prosthetic aortic valve from the delivery sheath includes releasing the prosthetic aortic valve from the delivery sheath, such that the prosthetic aortic valve transitions to the expanded fully-deployed configuration, in which the central longitudinal axis passes through a space surrounded by the prosthetic-valve coil.

Inventive Concept 22. The method according to Inventive Concept 18, further including rotationally orienting the prosthetic aortic valve such that the prosthetic-valve coil faces generally anterio-superiorly toward a sternum of the patient.

Inventive Concept 23. The method according to Inventive Concept 22, wherein when the prosthetic aortic valve is in the expanded fully-deployed configuration, (a) a downstream-most point of mechanical coupling between the prosthetic-valve coil and the frame and (b) a centroid of the cathode are rotationally aligned with each other or rotationally offset from each other about the central longitudinal axis by less than 50 degrees, and wherein rotationally orienting the prosthetic aortic valve includes aligning the cathode adjacent to cardiac tissue near a bundle of His of the patient, so as to automatically align the prosthetic-valve coil facing generally anterio-superiorly toward a sternum of the patient.

Inventive Concept 24. The method according to Inventive Concept 18, wherein releasing the prosthetic aortic valve from the delivery sheath includes releasing the prosthetic aortic valve from the delivery sheath, such that the prosthetic aortic valve transitions to the expanded fully-deployed configuration, the cathode is located upstream of the anode along the frame.

Inventive Concept 25. The method according to Inventive Concept 18, wherein releasing the prosthetic aortic valve from the delivery sheath includes releasing the prosthetic aortic valve from the delivery sheath, such that the prosthetic aortic valve transitions to the expanded fully-deployed configuration, in which the frame is shaped so as to define:

(a) an upstream inflow portion, (b) a downstream outflow portion, and (c) a constriction portion, which is axially between the upstream inflow portion and the downstream outflow portion, wherein the prosthetic leaflets are coupled to the constriction portion, and wherein when the prosthetic aortic valve is in the expanded fully-deployed configuration, free edges of the prosthetic leaflets face toward the downstream outflow portion, and wherein the cathode is coupled to the upstream inflow portion of the frame.

Inventive Concept 26. The method according to Inventive Concept 18, wherein releasing the prosthetic aortic valve from the delivery sheath includes releasing the prosthetic aortic valve from the delivery sheath, such that the prosthetic aortic valve transitions to the expanded fully-deployed configuration, in which the frame is shaped so as to define:

(a) an upstream inflow portion, (b) a downstream outflow portion, and (c) a constriction portion, which is axially between the upstream inflow portion and the downstream outflow portion, wherein the prosthetic leaflets are coupled to the constriction portion, and wherein when the prosthetic aortic valve is in the expanded fully-deployed configuration, (A) free edges of the prosthetic leaflets face toward the downstream outflow portion, and (B) a ring-shaped longitudinal border between the downstream outflow portion and the constriction portion is defined by a downstream-most point of the frame to which the prosthetic leaflets are coupled, and wherein a downstream-most point of mechanical coupling between the prosthetic-valve coil and the frame is located on the downstream outflow portion.

Inventive Concept 27. The method according to Inventive Concept 26, wherein an upstream-most point of mechanical coupling between the prosthetic-valve coil and the frame is located on the constriction portion.

Inventive Concept 28. The method according to Inventive Concept 18, further including activating external-unit control circuitry of an external unit, disposed outside a body of the patient, to drive an energy-transmission coil of the external unit to wirelessly transfer energy to the prosthetic-valve coil by inductive coupling.

Inventive Concept 29. The method according to Inventive Concept 28, further including positioning the energy-transmission coil against a chest of the patient, over a sternum of the patient.

Inventive Concept 30. The method according to Inventive Concept 28, further including positioning the energy-transmission coil around a neck of the patient.

Inventive Concept 31. The method according to Inventive Concept 28, wherein activating the external-unit control circuitry includes activating the external-unit control circuitry to drive the cathode and the anode to apply a pacing signal to a heart of the patient, by wirelessly transferring the energy from the energy-transmission coil to the prosthetic-valve coil by inductive coupling.

Inventive Concept 32. The method according to Inventive Concept 31, wherein activating the external-unit control circuitry includes activating the external-unit control circuitry to:

detect at least one cardiac parameter using a cardiac sensor, and at least partially responsively to the detected at least one cardiac parameter, set parameters of the pacing signal, by wirelessly transferring the energy from the energy-transmission coil to the prosthetic-valve coil by inductive coupling.

Inventive Concept 33. The method according to Inventive Concept 32, wherein the cardiac sensor includes at least two sensing skin ECG electrodes placed on skin of the patient.

Inventive Concept 34. The method according to Inventive Concept 28, wherein activating the external-unit control circuitry includes activating the external-unit control circuitry to wirelessly transfer the energy by generating a plurality of AC pulses, each including a train of AC bursts, and wherein the prosthetic aortic valve includes a passive diode, which is coupled in electrical communication with the prosthetic-valve coil, and is configured to rectify current in the prosthetic-valve coil.

Inventive Concept 35. The method according to Inventive Concept 34, wherein activating the external-unit control circuitry includes activating the external-unit control circuitry to generate the train of AC bursts at a frequency of between 3 kHz and 130 kHz.

Inventive Concept 36. The method according to Inventive Concept 34, wherein activating the external-unit control circuitry includes activating the external-unit control circuitry to include 20-100 AC bursts in each of the AC pulses.

The present invention will be more fully understood from the following detailed description of embodiments thereof, taken together with the drawings, in which:

DETAILED DESCRIPTION OF APPLICATIONS

Figure 1:
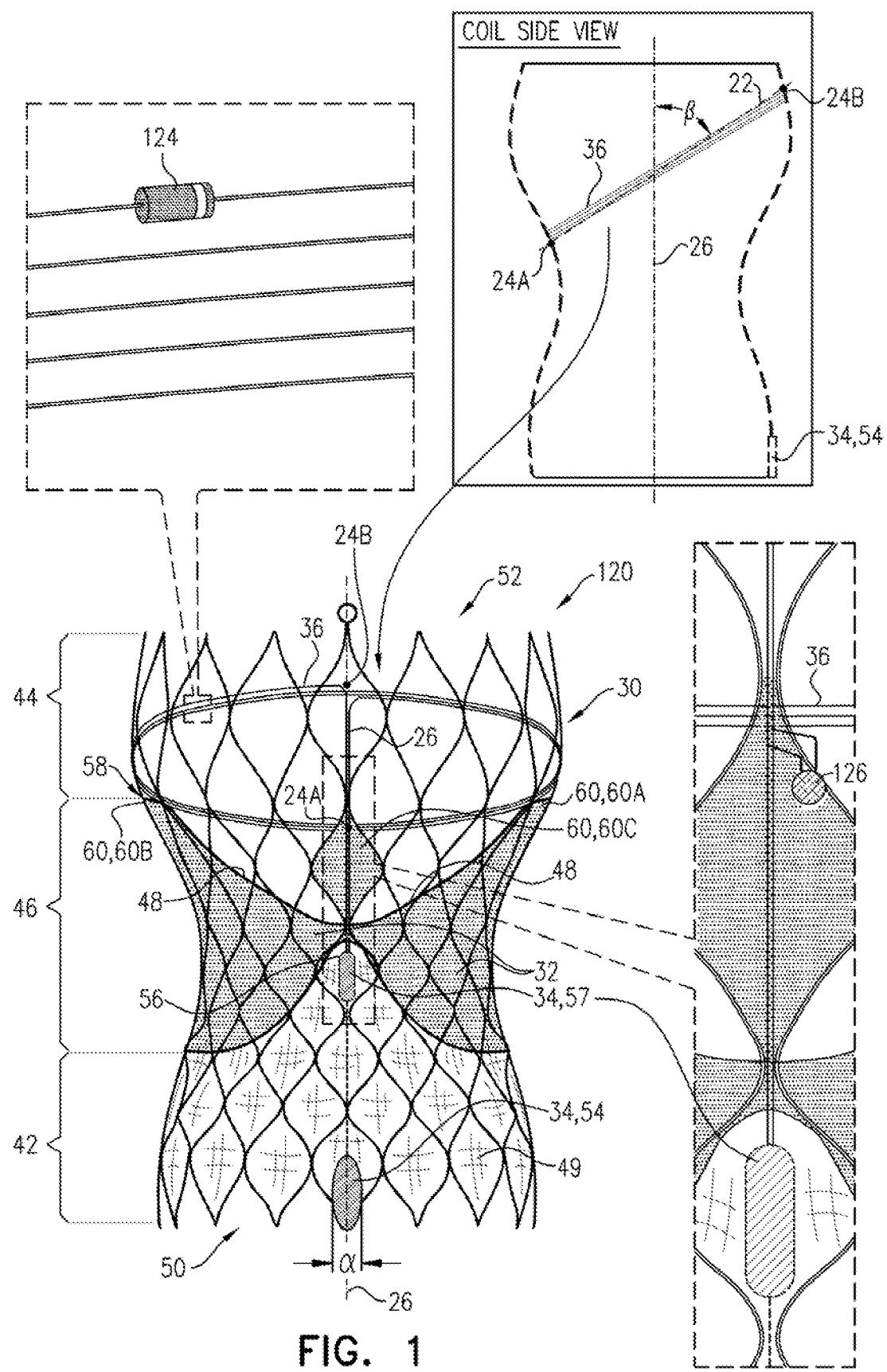
FIG. 1 is a schematic illustration of a prosthetic aortic valve, in accordance with an application of the present invention.

Reference is made to FIG. 1, which is a schematic illustration of a prosthetic aortic valve 20, in accordance with an application of the present invention.

Figure 2:
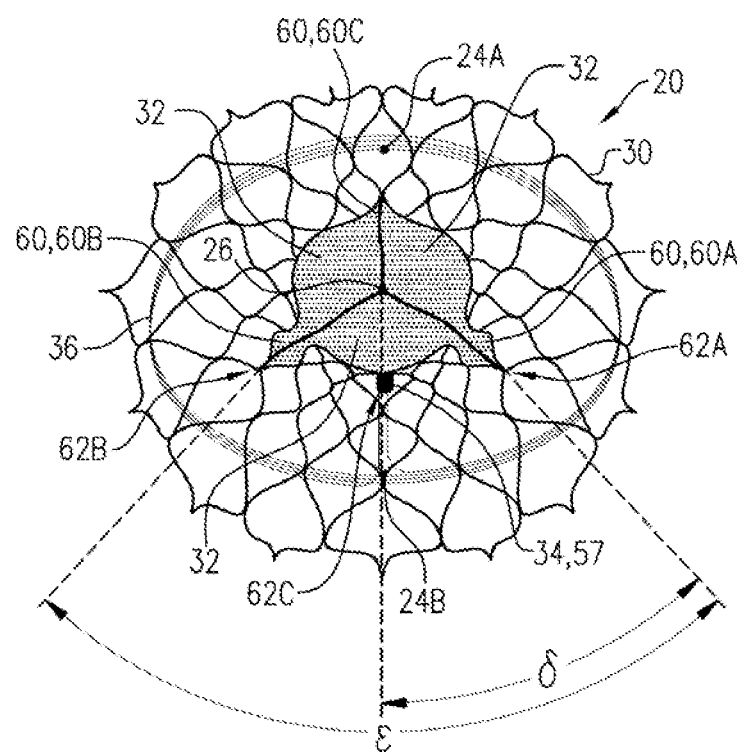
FIG. 2 is a schematic illustration of the prosthetic aortic valve of FIG. 1 viewed from a downstream outflow end of the prosthetic aortic valve, in accordance with an application of the present invention.

Reference is also made to FIG. 2, which is a schematic illustration of prosthetic aortic valve 20 viewed from a downstream outflow end 52 of prosthetic aortic valve 20, as described hereinbelow, in accordance with an application of the present invention.

Prosthetic aortic valve 20 is shown in FIGS. 1 and 2 in an expanded configuration, which is similar to the expanded fully-deployed configuration described hereinbelow with reference to FIGS. 6C-D, except that in FIGS. 1 and 2 expansion of prosthetic aortic valve 20 is not limited by anatomy of a patient.

Prosthetic aortic valve 20 comprises:
a frame 30;
a plurality of prosthetic leaflets 32 coupled to frame 30;
electrodes 34, which include a cathode 54 and an anode 57, and which are mechanically coupled to frame 30; and
a prosthetic-valve coil 36 coupled to frame 30 in non-wireless electrical communication with cathode 54 and anode 57.

Frame 30 typically comprises a stent or other structure, which is typically self-expanding, and may be formed by laser cutting or etching a metal alloy tube comprising, for example, stainless steel or a shape memory material such as Nitinol. For some applications, one or more of electrodes 34 are coupled to frame 30 using techniques described in U.S. Pat. No. 9,526,637 to Dagan et al. and/or US 2016/0278951 to Dagan et al., both of which are incorporated herein by reference. For some applications, prosthetic-valve coil 36 comprises gold wire, in order to provide low resistance.

Prosthetic-valve coil 36 may be coupled to frame 30 either inside the frame or outside the frame, or partially inside and partially outside the frame.

Prosthetic aortic valve 20 is configured to be delivered to a native aortic valve of a patient in a constrained delivery configuration within a delivery sheath 72, such as described hereinbelow with reference to FIGS. 6A-B.

For some applications, when prosthetic aortic valve 20 is in an expanded fully-deployed configuration upon release from delivery sheath 72, such as shown in FIGS. 1, 2, and 6C-D, (a) a line 22 defined between upstream-most and downstream-most points 24A and 24B of mechanical coupling between prosthetic-valve coil 36 and frame 30 and (b) a central longitudinal axis 26 defined by frame 30 form an angle β (beta) of between 20 and 70 degrees, such as between 30 and 60 degrees, e.g., between 40 and 50 degrees, such as 45 degrees. This angle provides good coupling between prosthetic-valve coil 36 and an energy-transmission coil, such as described hereinbelow with reference to FIG. 6D.

For some applications, when prosthetic aortic valve 20 is in the expanded fully-deployed configuration, such as shown in FIGS. 1, 2, and 6C-D, central longitudinal axis 26 passes through a space surrounded by prosthetic-valve coil 36, such as shown in the figures.

Alternatively or additionally, for some applications, prosthetic-valve coil 36 is shaped so as to define a best-fit plane that forms angle β (beta) with central longitudinal axis 26 of frame 30.

As used in the present application, including in the claims and Inventive Concepts, the "central longitudinal axis" 26 of frame 30 is the set of all centroids of transverse cross-sectional sections of frame 30 along frame 30. Thus the cross-sectional sections are locally perpendicular to the central longitudinal axis, which runs along frame 30. (For applications in which frame 30 is circular in cross-section, the centroids correspond with the centers of the circular cross-sectional sections.) As used in the present application, including in the claims and Inventive Concepts, a "best-fit plane" is the plane that most closely matches the shape of prosthetic-valve coil 36, i.e., the plane that results in the minimal sum of squares of distances between the plane and prosthetic-valve coil 36. As used in the present application, including in the claims and Inventive Concepts, an angle between two lines or between a line and a plane is the smaller of the two supplementary angles between the two lines or the line and the plane, or equals 90 degrees if the two lines or the line and the plane are perpendicular.

This angling of prosthetic-valve coil 36 with respect to central longitudinal axis 26 of frame 30 allows more compact crimping (compression) of prosthetic-valve coil 36 into delivery sheath 72, such as described hereinbelow with reference to FIGS. 6A-B, than in an alternate configuration in which prosthetic-valve coil 36 is perpendicular to central longitudinal axis 26 of frame 30, because the metal of prosthetic-valve coil 36 is more axially distributed along frame 30.

For other applications, prosthetic-valve coil 36 is angled at a different angle with respect to central longitudinal axis 26 of frame 30. For example, prosthetic-valve coil 36 may be perpendicular to central longitudinal axis 26 of frame 30, such as shown in FIG. 1A of US Patent Application Publication 2020/0261224 to Gross, which is incorporated herein by reference.

For some applications, when prosthetic aortic valve 20 is in the expanded fully-deployed configuration, such as shown in FIGS. 1, 2, and 6C-D (a) downstream-most point 24B of mechanical coupling between prosthetic-valve coil 36 and frame 30 and (b) a centroid 28 of cathode 54 are rotationally aligned with each other or rotationally offset from each other about central longitudinal axis 26 by less than 50 degrees, such as less than 30 degrees. A reason for this rotational alignment is provided hereinbelow with reference to FIGS. 6B and 6D.

For some applications, cathode 54 is located upstream of anode 57 along frame 30.

For some applications, cathode 54 and anode 57 are used for bipolar sensing and/or pacing, as known in the art.

For some applications, cathode 54 and anode 57 are disposed on frame 30 such that there is at least 15 mm between the cathode and the anode, when prosthetic aortic valve 120 is in the expanded fully-deployed configuration described hereinbelow with reference to FIGS. 6C-D (the 15 mm is measured along central longitudinal axis 26 of frame 30 when in the expanded fully-deployed configuration).

For some applications, respective non-electrically-insulated end portions of prosthetic-valve coil 36 define cathode 54 and anode 57. In these applications, prosthetic aortic valve 20 typically does not comprise elongate insulated electrical conductors, described hereinbelow with reference to FIG. 4. Instead, respective insulated end portions of prosthetic-valve coil 36 bend away from prosthetic-valve coil 36 along the paths of elongate insulated electrical conductors 138 described hereinbelow with reference to FIG. 5, such that the respective non-electrically-insulated end portions of prosthetic-valve coil 36 are located at the locations at which cathode 54 and anode 57 are shown in FIG. 1, respectively.

For other applications, prosthetic aortic valve 20 further comprises one or more elongate insulated electrical conductors 138, e.g., wires, which couple prosthetic-valve coil 36 in the non-wireless electrical communication with cathode 54 and anode 57, such as described hereinbelow with reference to FIG. 5, mutatis mutandis.

For some applications, prosthetic aortic valve 20 does not comprise any active electronic components.

For some applications, when prosthetic aortic valve 20 is in the expanded fully-deployed configuration, frame 30 is shaped so as to define an upstream inflow portion 42, a downstream outflow portion 44, and a constriction portion 46, which is axially between upstream inflow portion 42 and downstream outflow portion 44. Prosthetic leaflets 32 are coupled to constriction portion 46 such that free edges 48 of prosthetic leaflets 32 face toward downstream outflow portion 44 when prosthetic aortic valve 20 is in the expanded fully-deployed configuration described hereinbelow with reference to FIGS. 6C-D. Prosthetic leaflets 32 are not coupled to downstream outflow portion 44; therefore, a ring-shaped longitudinal border 58 between downstream outflow portion 44 and constriction portion 46 is defined by a downstream-most point of frame 30 to which prosthetic leaflets 32 are coupled (for example, prosthetic leaflets 32 may be coupled to the downstream-most point of frame 30 at commissures 60, described immediately hereinbelow). (Ring-shaped longitudinal border 58 is at the same longitudinal location around frame 30.) Typically, prosthetic aortic valve 20 further comprises a skirt 49 coupled to upstream inflow portion 42 of frame 30, and prosthetic leaflets 32 are attached along their bases to skirt 49, for example, using sutures or a suitable biocompatible adhesive. Adjoining pairs of leaflets are attached to one another at their lateral ends to form commissures 60, with free edges 48 of the prosthetic leaflets forming coaptation edges that meet one another. Skirt 49 and prosthetic leaflets 32 typically comprise a sheet of animal pericardial tissue, such as porcine pericardial tissue, or synthetic or polymeric material.

For some applications, cathode 54 is coupled to upstream inflow portion 42 of frame 30.

For some applications, cathode 54 has a lateral dimension a (alpha), measured in degrees around frame 30 with respect to central longitudinal axis 26 of frame 30, of between 10 and 40 degrees, e.g., between 20 and 40 degrees, such as 30 degrees, in order to accommodate rotational misplacement of frame 30 with respect to the bundle of His. Typically, prosthetic aortic valve 20 is deployed using imaging, such as fluoroscopy, and is rotated if necessary during the deployment such that cathode 54 is disposed against tissue of the annulus that is near the bundle of His. For some applications, prosthetic aortic valve 20 comprises a plurality of cathodes 54 (e.g., two or three, or more), which are disposed at a respective plurality of angular locations around frame 30 (e.g., 10-15 degrees apart). After implantation of prosthetic aortic valve 20, the cathode 54 that has the most accurate angular location is activated to apply a pacing signal and/or sense, either by (a) external control circuitry, such as external-unit control circuitry 104, described hereinbelow with reference to FIG. 6D, or (b) prosthetic-aortic-valve control circuitry 140, if provided, such as described hereinbelow with reference to FIG. 5. Alternatively or additionally, for some applications, cathode 54 has an axial length of at least 10 mm, in order to accommodate axial misplacement of frame 30 with respect to the annulus of the natural aortic valve, and thus with respect to the bundle of His. As used in the present application, including in the claims and Inventive Concepts, an "axial length" is a length of a structure measured along central longitudinal axis 26.

For some applications, cathode 54 has a thickness of between 75 and 125 microns, e.g., about 100 microns, and/or a surface area of at least 2.5 mm2, in order to provide adequate stimulation. For some applications, cathode 54 comprises titanium nitride (TiN). For some applications, skirt 49 is coupled to an external surface of upstream inflow portion 42 of frame 30, and cathode 54 is disposed on an external surface of skirt 49.

For some applications, when prosthetic aortic valve 20 is in the expanded fully-deployed configuration described hereinbelow with reference to FIGS. 6C-D:

frame 30 has an inflow end 50 at upstream inflow portion 42 and downstream outflow end 52 at downstream outflow portion 44, and an axial length, measured between inflow end 50 and downstream outflow end 52, and at least one of (e.g., exactly one of, e.g., cathode 54) the one or more electrodes 34 is coupled to upstream inflow portion 42 within a distance from inflow end 50, the distance equal to 10% of the axial length of frame 30 (the distance is measured (a) along central longitudinal axis 26 of frame 30 when in the expanded fully-deployed configuration, and (b) between inflow end 50 and an upstream-most point of the at least one electrode).

For some applications, downstream-most point 24B of mechanical coupling between prosthetic-valve coil 36 and frame 30 is located on downstream outflow portion 44 when prosthetic aortic valve 20 is in the expanded fully-deployed configuration.

For some applications, upstream-most point 24A of mechanical coupling between prosthetic-valve coil 36 and frame 30 is located on constriction portion 46 when prosthetic aortic valve 20 is in the expanded fully-deployed configuration.

For some applications, prosthetic leaflets 32 are coupled to frame 30 at at least first and second commissures 60A and 60B of prosthetic aortic valve 20 that are located at respective first and second angular locations 62A and 62B around frame 30. The first and second angular locations 62A and 62B are separated by a first angular offset ε (epsilon) around frame 30 (labeled in FIG. 2) when prosthetic aortic valve 20 is in the expanded fully-deployed configuration described hereinbelow with reference to FIGS. 6C-D. Cathode 54 is coupled to frame 30 at a third angular location 62C around frame 30 that is separated from first angular location 62A by a second angular offset δ (delta) that equals between 40% and 60% (e.g., 50%) of the first angular offset ε (epsilon) when prosthetic aortic valve 20 is in the expanded fully-deployed configuration described hereinbelow with reference to FIG. 6C-D. At the third angular location 62C around frame 30, the frame is more flexible than at the more rigid commissures. As used in the present application, including in the claims and Inventive Concepts, an "angular location" is a location on frame 30 at a particular location around central longitudinal axis 26, i.e., at a particular "o'clock" with respect to central longitudinal axis 26. (It is noted that a third commissure 60C is shown in FIG. 1A on the far side of the frame, i.e., 180 degrees from cathode 54.)

Figure 3:
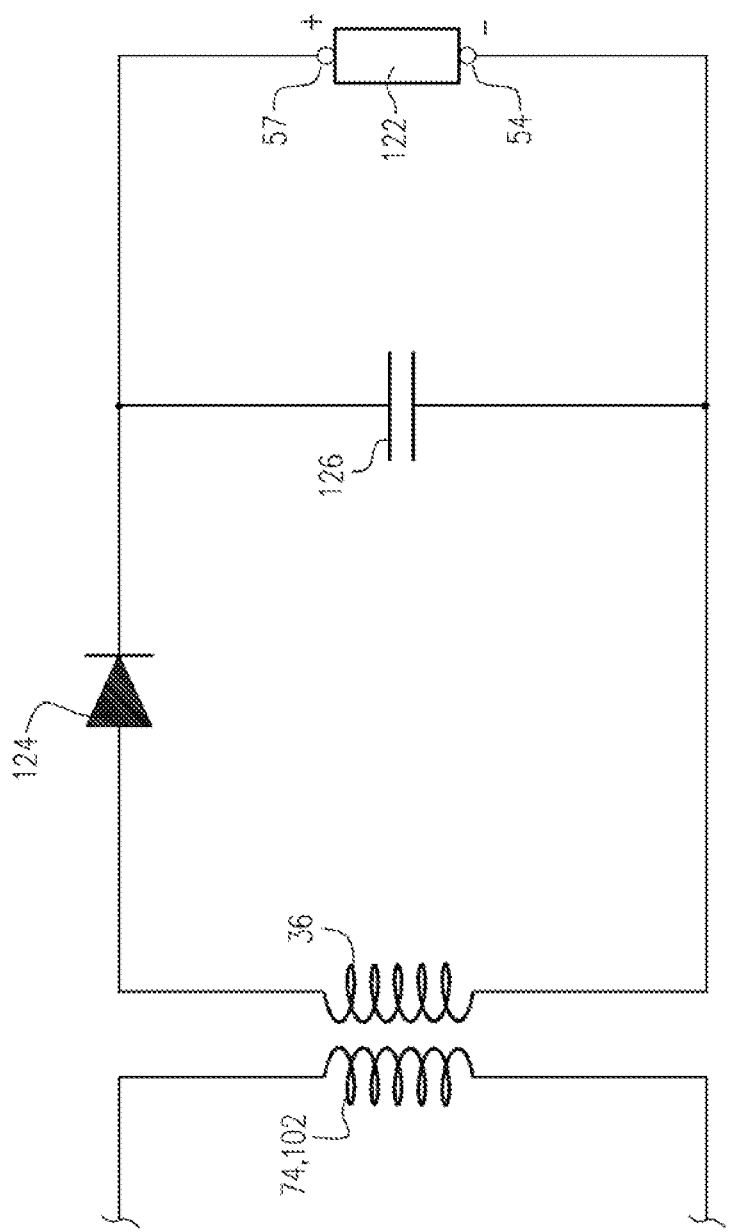
FIG. 3 is a schematic illustration of passive electrical components of the prosthetic aortic valve of FIG. 1 and tissue, in accordance with an application of the present invention.

Reference is again made to FIG. 1, and is additionally made to FIG. 3, which is a schematic illustration of passive electrical components of prosthetic aortic valve 20 and tissue 122, in accordance with an application of the present invention. Tissue 122 includes cardiac tissue and blood. Cathode 54 is configured to be in contact with the cardiac tissue, and anode 57 is configured to be in contact with the blood. As is known in the art, cardiac tissue acts as a resistor.

For some applications, prosthetic aortic valve 20 comprises a passive diode 124 (shown highly schematically in the upper exploded view in FIG. 1, as well as in FIG. 3), which is coupled in electrical communication with prosthetic-valve coil 36 and rectifies current in prosthetic-valve coil 36. For example, the diode may be positioned at one end of the coil or adjacent to cathode 54 or anode 57, or (as shown in FIG. 1) at some point along prosthetic-valve coil 36. External-unit control circuitry 104 (shown in FIG. 6D) typically wirelessly transfers energy to prosthetic-valve coil 36 by generating a plurality of AC pulses, each AC pulse including a train of AC bursts. The train of AC bursts may be generated, for example, at a frequency of between 3 kHz and 130 kHz (e.g., between 3 kHz and 100 kHz, or between 100 kHz and 130 kHz), for improved efficiency. For some applications, there are 20-100 AC bursts in each of the AC pulses. Other frequencies and number of bursts are within the scope of the present invention.

For some applications, prosthetic aortic valve 120 comprises exactly one passive diode 124, which provides half-wave rectification of the AC pulses. For other applications, prosthetic aortic valve 120 comprises a plurality of passive diode 124, which provides full-wave rectification of the AC pulses; for example, prosthetic aortic valve 120 may comprise four passive diodes 124 arranged in a bridge configuration, as is known in the electronics arts.

For some applications, prosthetic aortic valve 20 comprises a capacitor 126 (shown highly schematically in the exploded view to the right in FIG. 1, as well as in FIG. 3), which is in electrical communication with cathode 54 and anode 57 (parallel to tissue 122 in the circuit made upon implantation of the electrodes). Capacitor 126 typically increases the efficiency of the circuit by delivering a larger proportion of the received energy into tissue 122. (As is known in the electronics art, a capacitor is a passive electrical component.)

Optionally, prosthetic aortic valve 120 comprises additional passive electrical components, such as one or more resistors.

Figure 4:
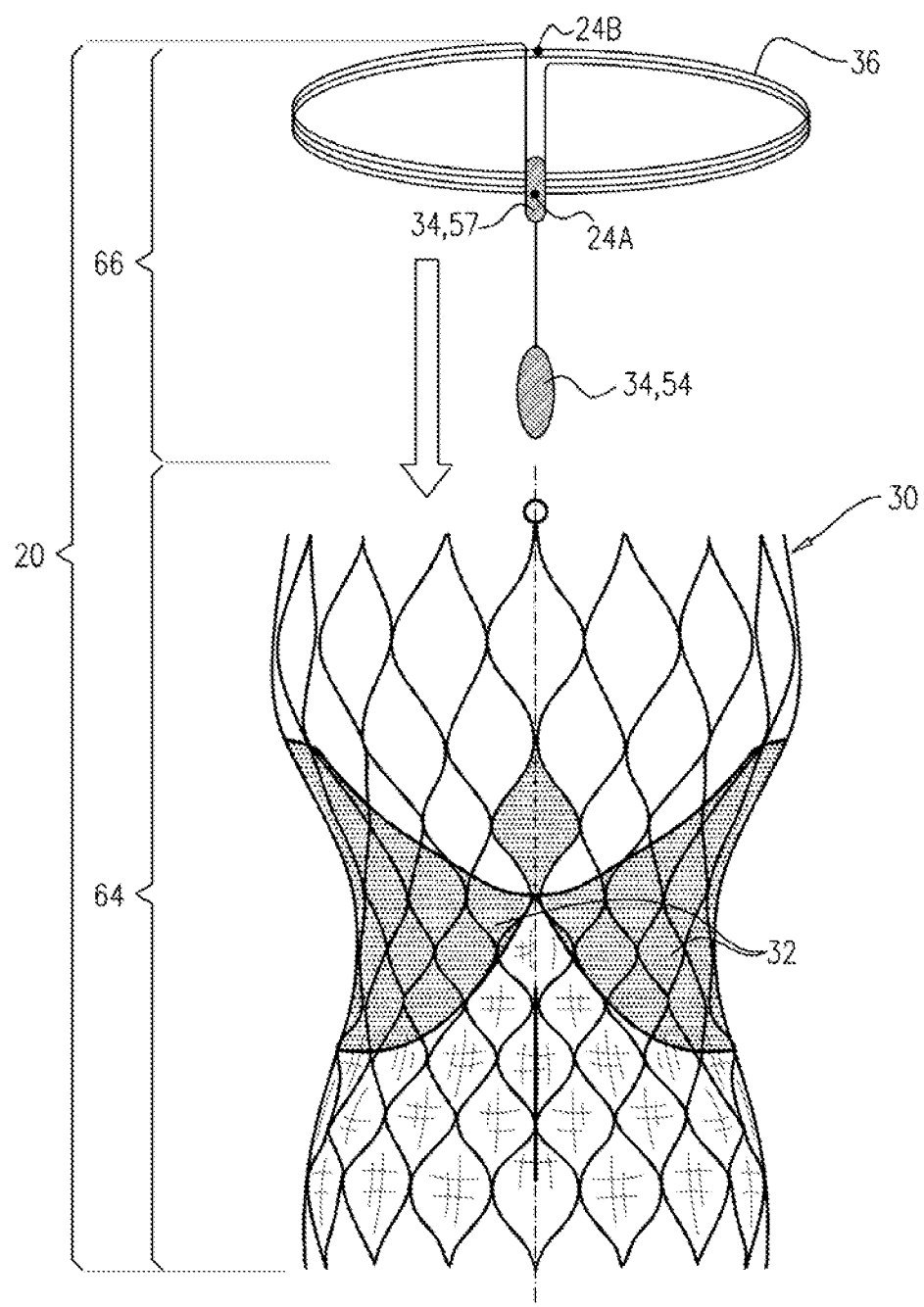
FIG. 4 is a schematic illustration of components of the prosthetic aortic valve of FIG. 1 before complete assembly, in accordance with an application of the present invention.

Reference is now made to FIG. 4, which is a schematic illustration of components of prosthetic aortic valve 20 before complete assembly, in accordance with an application of the present invention. The components comprise a valve component 64 and an electronics component 66. Valve component 64 typically consists of a heart valve prosthesis known in the art, which comprises at least frame 30 and prosthetic leaflets 32. For example, the known heart valve prosthesis may comprise a CoreValve™ Evolut™ R prothesis (Medtronic, Inc., Minneapolis, Minn., USA), a CoreValve™ Evolut™ PRO prosthesis (Medtronic, Inc.), a LOTUS Edge™ Aortic Valve (Boston Scientific Corporation, Marlborough, Mass., USA), or an ACURATE Neo™ Aortic Valve (Boston Scientific Corporation). Electronics component 66 comprises at least the one or more electrodes 34 and prosthetic-valve coil 36, and optionally, in the configuration described hereinbelow with reference to FIG. 5, prosthetic-aortic-valve control circuitry 140.

During assembly of prosthetic aortic valve 20, electronics component 66 is inserted into valve component 64. For some applications, a first portion of electronics component 66, such as prosthetic-valve coil 36 and one of the one or more electrodes 34, is coupled to an inner surface of frame 30, and a second portion of electronics component 66, such as cathode 54, is coupled to an external surface of frame 30. For example, one of the non-electrically-insulated end portions of prosthetic-valve coil 36 may (a) electrically couple prosthetic-valve coil 36 to cathode 54 and (b) pass from inside to outside frame 30, typically through skirt 49. (Coupling one of the one or more electrodes 34 to the inner surface of frame 30 may expose the electrode to blood of the subject upon implantation of the assembled prosthetic aortic valve 20. Coupling cathode 54 to the external surface of frame 30 may dispose the cathode against tissue, such as tissue of the annulus that is near the bundle of His, upon implantation of the assembled prosthetic aortic valve 20, such as described herein.) Optionally, the components of electronics component 66 may be stitched to frame 30 and/or skirt 49.

For some applications, whether prosthetic-valve coil 36 is coupled to an inner or an external surface of frame 30, prosthetic-valve coil 36 is electrically isolated from frame 30, such as by isolation material (e.g., a sheet of material or a coating) disposed between prosthetic-valve coil 36 and frame 30. For example, the isolation material may comprise a non-conductive polymer.

The above-mentioned assembly of prosthetic aortic valve 20 is typically performed in a manufacturing facility, and thereafter the assembled prosthetic aortic valve 20 is packaged and shipped to a healthcare facility for implantation. The method of assembling prosthetic aortic valve 20 is thus non-surgical.

Figure 5:
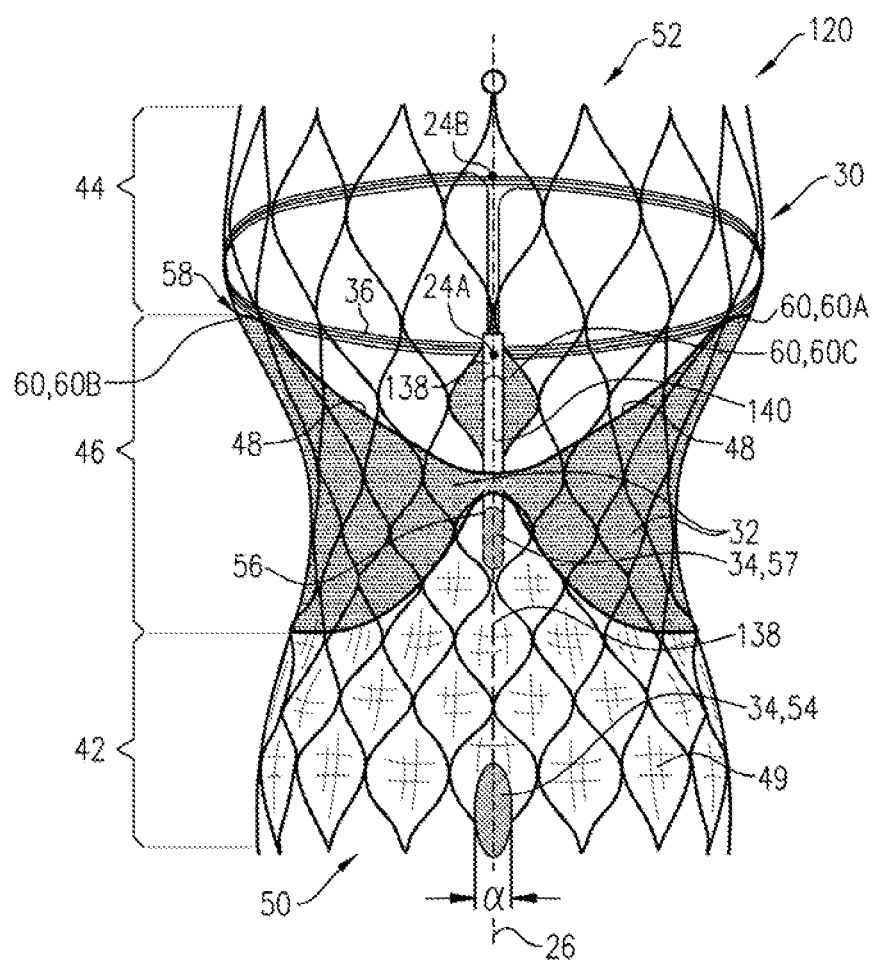
FIG. 5 is a schematic illustration of another prosthetic aortic valve, in accordance with an application of the present invention.

Reference is now made to FIG. 5, which is a schematic illustration of a prosthetic aortic valve 120, in accordance with an application of the present invention. Prosthetic aortic valve 120 is shown in FIG. 5 in an expanded configuration, which is similar to the expanded fully-deployed configuration of prosthetic aortic valve 20 described hereinbelow with reference to FIGS. 6C-D, except that in FIG. 5 expansion of prosthetic aortic valve 120 is not limited by anatomy of a patient. Other than as described hereinbelow, prosthetic aortic valve 120 is identical to prosthetic aortic valve 20 described herein with reference to FIGS. 1-4, and like reference numerals refer to like parts. Prosthetic aortic valve 120 may be assembled as described hereinabove with reference to FIG. 4 for prosthetic aortic valve 20, mutatis mutandis.

Prosthetic aortic valve 120 further comprises prosthetic-aortic-valve control circuitry 140, which is coupled to frame 30 and which is in non-wireless electrical communication with the one or more electrodes 34. In these applications, prosthetic-valve coil 36 is in non-wireless electrical communication with prosthetic-aortic-valve control circuitry 140, such that prosthetic-valve coil 36 is in non-wireless electrical communication with the one or more electrodes 34 via prosthetic-aortic-valve control circuitry 140. One or more of the one or more electrodes 34 may be directly attached in non-wireless electrical communication to prosthetic-aortic-valve control circuitry 140, and/or may be attached in non-wireless electrical communication to prosthetic-aortic-valve control circuitry 140 by the one or more elongate insulated electrical conductors 138. Typically, prosthetic-aortic-valve control circuitry 140 is flexible, and has a thin, linear packaging, and may implement, mutatis mutandis, techniques described with reference to FIG. 5 of US Patent Application Publication 2020/0261224, which is incorporated herein by reference. The thinness of control circuitry 140 allows it to be compressed in delivery sheath 72 during deployment of prosthetic aortic valve 120, without the need to increase the diameter of the delivery sheath. In addition, the flexibility of control circuitry 140 prevents damage to the control circuitry when it is crimped when compressed into the delivery sheath.

Typically, prosthetic-aortic-valve control circuitry 140 is coupled to frame 30 such that upstream-most point of prosthetic-aortic-valve control circuitry 140 is disposed axially along constriction portion 46 and/or downstream outflow portion 44 of frame 30.

Typically, prosthetic-aortic-valve control circuitry 140 is coupled to frame 30 inside frame 30, which may prevent friction between prosthetic-aortic-valve control circuitry 140 and delivery sheath 72 during deployment of prosthetic aortic valve 20, described hereinbelow with reference to FIGS. 6A-D regarding prosthetic aortic valve 20, mutatis mutandis.

For some applications, prosthetic-aortic-valve control circuitry 140 is coupled to frame 30 at third angular location 62C around frame 30, described hereinabove with reference to FIG. 2.

Figure 6A:
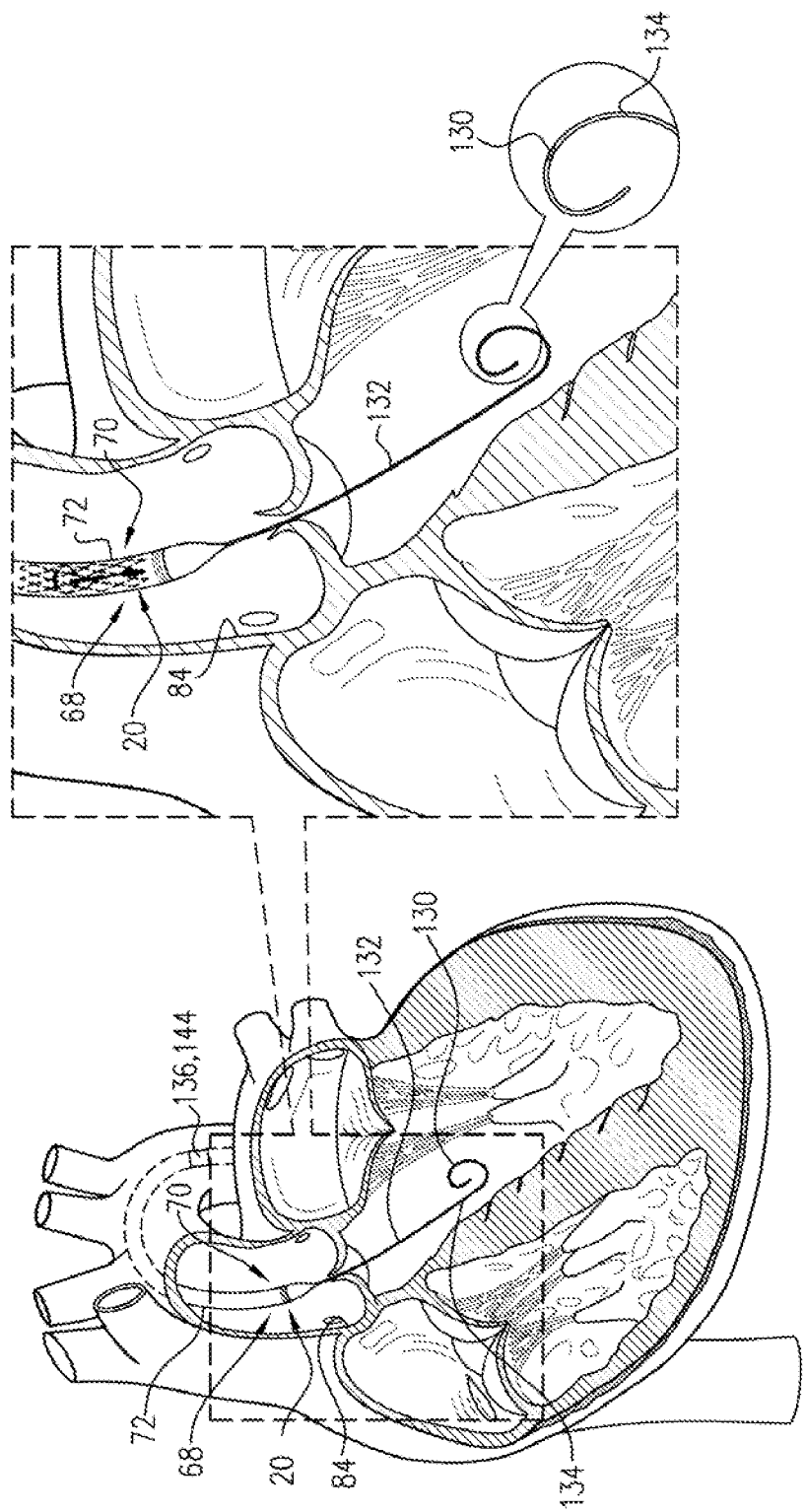
FIGS. 6A-D are schematic illustrations of a valve prosthesis system and a method of using the system, in accordance with respective applications of the present invention.
Figure 6B:
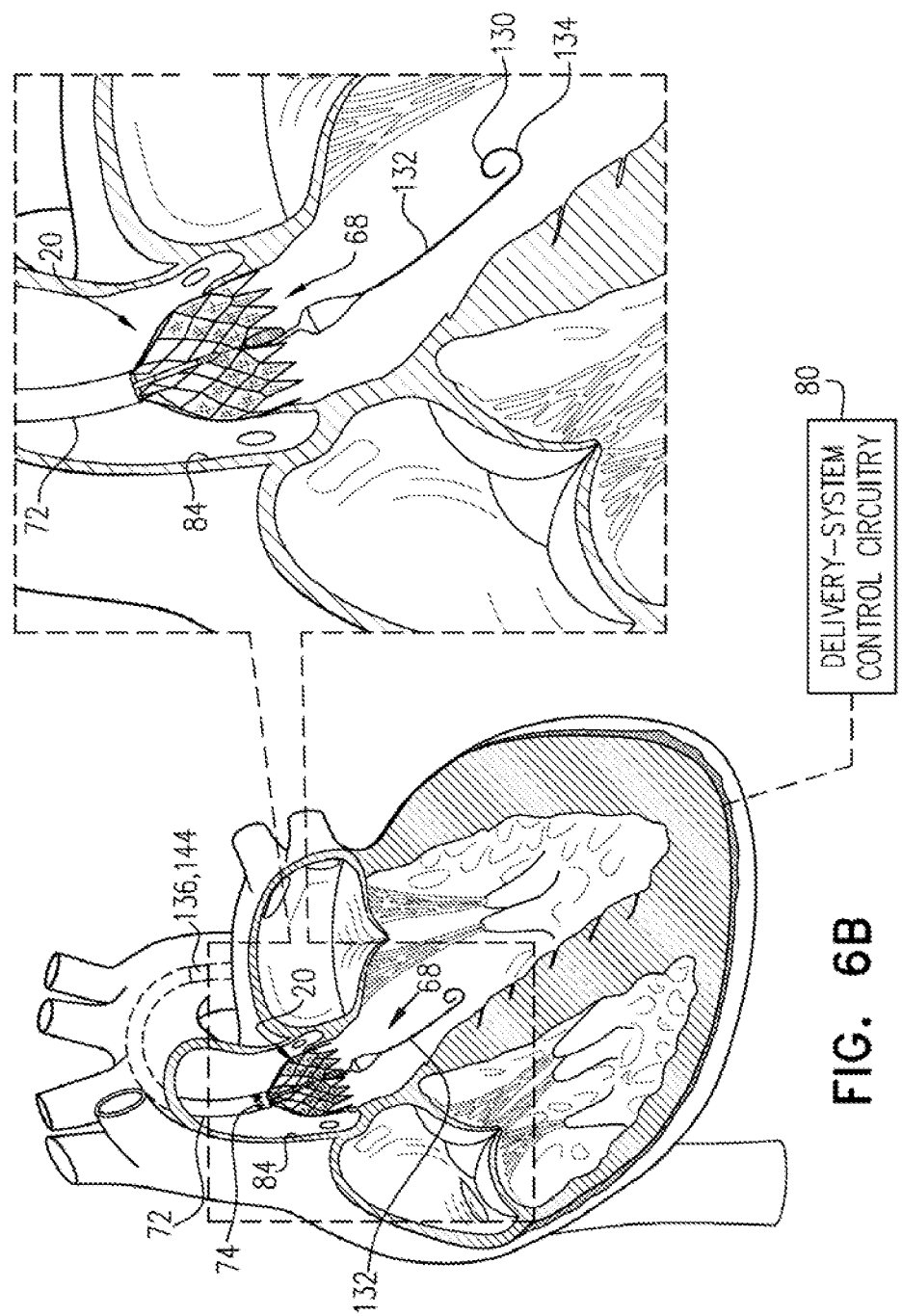
Figure 6C:
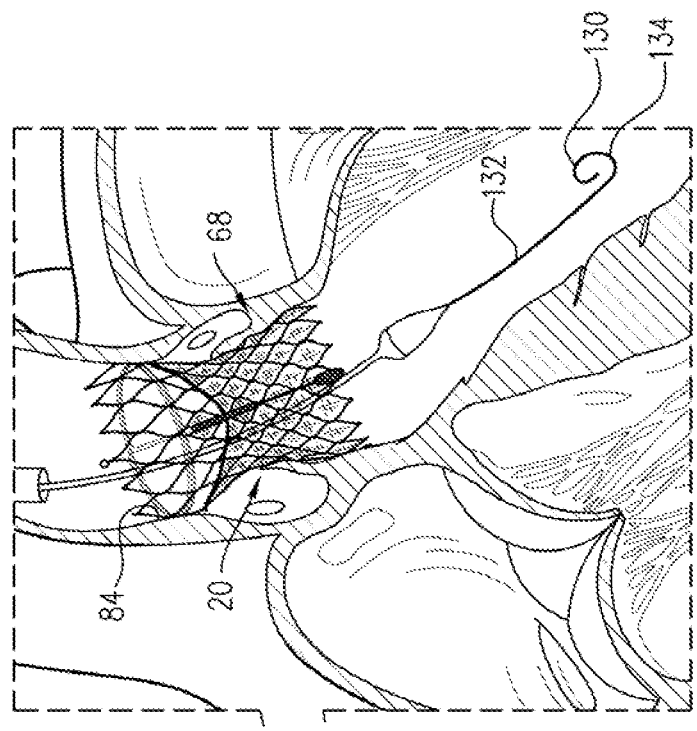
Figure 6C:
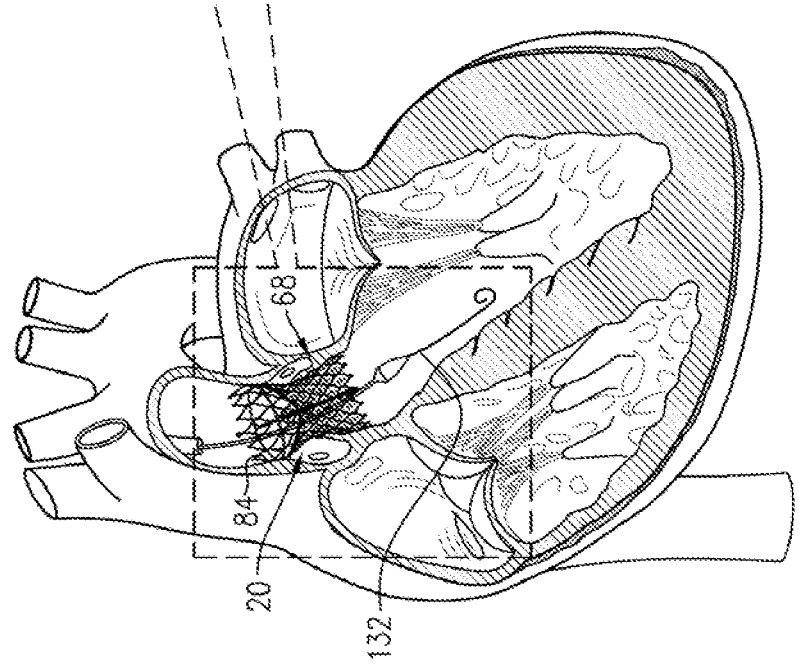
Figure 6D:
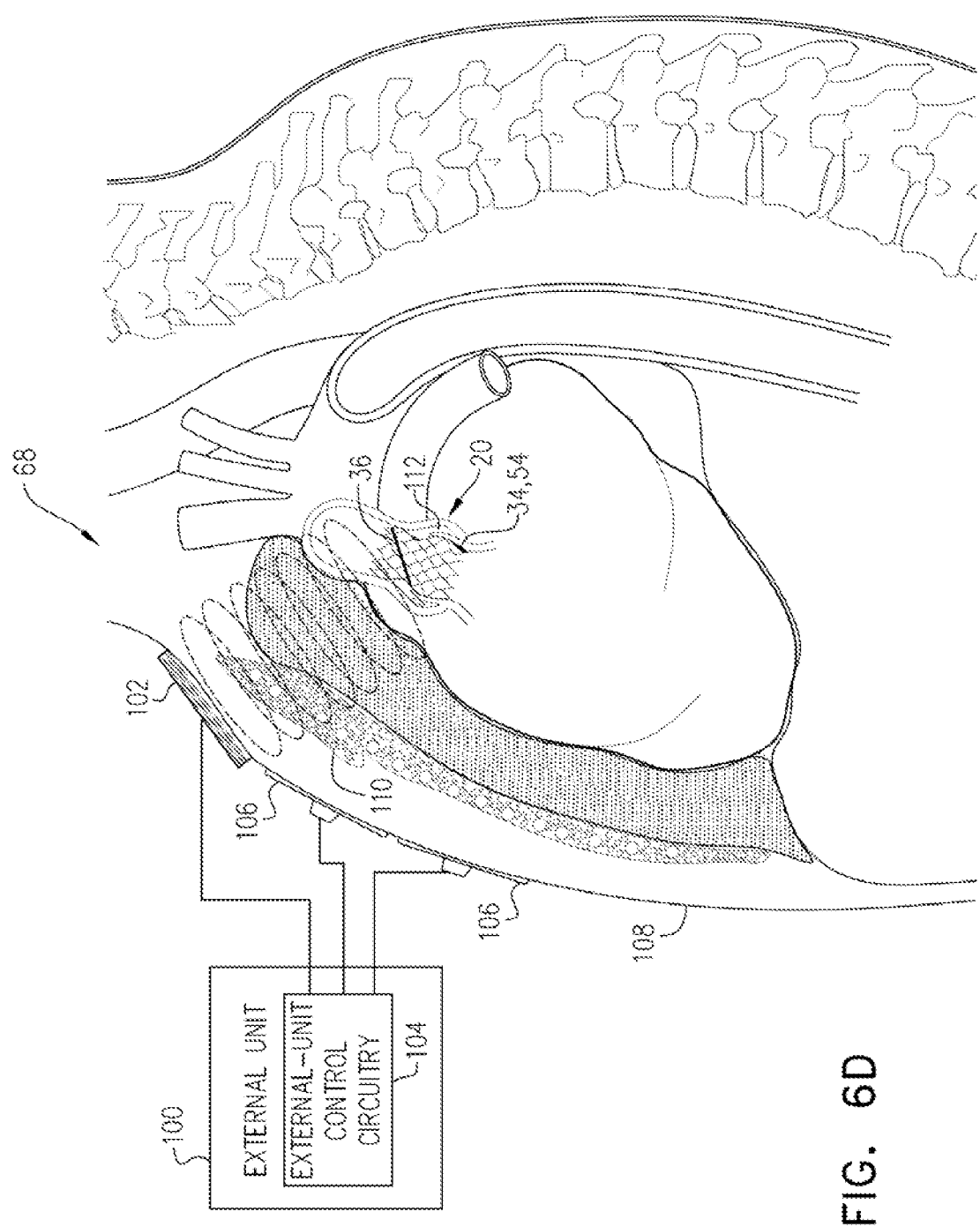

Reference is now made to FIGS. 6A-D, which are schematic illustrations of a valve prosthesis system 68 and a method of using the system, in accordance with respective applications of the present invention. Although the techniques described with reference to FIGS. 6A-D are generally described regarding prosthetic aortic valve 20, the techniques are equally applicable to prosthetic aortic valve 120, mutatis mutandis. The rotational orientation of the prosthetic aortic valve is shown schematically in FIGS. 6A-C, in order to illustrate the components of the prosthetic aortic valve; as described below, in actual use, the prosthetic aortic valve is typically rotationally oriented such that cathode 54 is positioned adjacent to cardiac tissue near the bundle of His, such as shown in FIG. 6D.

Valve prosthesis system 68 comprises (a) prosthetic aortic valve 20 or prosthetic aortic valve 120 and (b) a delivery system 70.

Delivery system 70 comprises:
delivery sheath 72;
one or more wires 78, which pass along delivery sheath 72, e.g., attached to an outer or inner surface of delivery sheath 72, or embedded in the wall of delivery sheath 72; and
optionally, delivery-system control circuitry 80, which is in electrical communication with delivery-system coil 74 via the one or more wires 78.

As shown in FIG. 6A, prosthetic aortic valve 20 is removably disposable in delivery sheath 72 in a compressed delivery configuration. During an implantation procedure, delivery sheath 72 is advanced through vasculature of a patient, until distal end 82 of delivery sheath 72 is disposed in an ascending aorta 84 of the patient, while prosthetic aortic valve 20 is removably disposed in delivery sheath 72 in the compressed delivery configuration.

As described hereinabove with reference to FIGS. 1-3, for some applications, the one or more electrodes 34 comprise cathode 54 that is coupled to upstream inflow portion 42 of frame 30. Before deployment, the prosthetic aortic valve is rotated (such as under guidance using imaging, e.g., fluoroscopy, such as of a marker on delivery sheath 72) such that cathode 54 is positioned adjacent to cardiac tissue near the bundle of His (near a non-coronary cusp 112 of the native aortic valve (labeled in FIG. 6D)), in order to pace the heart by stimulating the cardiac tissue with cathodic current.

Because of the rotational alignment of angled prosthetic-valve coil 36 with respect to cathode 54 described hereinabove with reference to FIGS. 1-2, the alignment of cathode 54 adjacent to cardiac tissue near the bundle of His (facing generally posteriorly) automatically aligns prosthetic-valve coil 36 facing generally in the opposite direction, facing generally anterio-superiorly, such as shown in FIG. 6D. This orientation provides good wireless coupling with an energy-transmission coil 102, such as described hereinbelow with reference to FIG. 6D.

For some applications, delivery system 70 comprises a cathode 130 separate from prosthetic aortic valve 20 or prosthetic aortic valve 120. For some applications, the separate cathode is disposed on a guidewire 132 used to introduce prosthetic aortic valve 20 or prosthetic aortic valve 120 into the native aortic valve. For example, cathode 130 may be located on a pigtail 134 of guidewire 132. To this end, pigtail 134 may optionally comprise an internal electrically-conductive wire coated with a non-conductive insulation, and cathode 130 may be defined by a non-insulated portion of pigtail 134. Delivery system 70 is configured to use this guidewire cathode 130 for applying rapid ventricular pacing (rather than cathode 54 of prosthetic aortic valve 20 or prosthetic aortic valve 120). In this case, cathode 54 of prosthetic aortic valve 20 or prosthetic aortic valve 120 is still typically used for applying post-implantation chronic pacing using external unit 100, such as described below.

For some applications, such as those in which delivery system 70 comprises cathode 130 separate from prosthetic aortic valve 20 or prosthetic aortic valve 120, delivery system 70 comprises an anode 136 separate from prosthetic aortic valve 20 or prosthetic aortic valve 120, and is configured to use this separate anode 136 for applying rapid ventricular pacing (rather than anode 57 of prosthetic aortic valve 20 or prosthetic aortic valve 120). In this case, anode 57 of prosthetic aortic valve 20 or prosthetic aortic valve 120 is still typically used for applying post-implantation chronic pacing using external unit 100, such as described below.

For some applications, the separate anode 136 of delivery system 70 comprises:
- a skin electrode 142 (shown in FIGS. 8 and 9B, described hereinbelow), e.g., a patch electrode, configured to be placed on skin of the patient; the patch electrode may have a relatively large surface area, e.g., a diameter of 6 to 10 cm (e.g., 8 cm), in order to provide good conduction; optionally, the patch electrode is incorporated into shirt 300, described hereinbelow with reference to FIGS. 9A-B (such as embedded into the shirt, or attached to an inner surface of the shirt),
- a sheath electrode 144, e.g., a conductive coating, disposed along delivery sheath 72, such as along a proximal portion of the sheath that is configured to be disposed in the aorta, e.g., the descending aorta, when distal end 82 of delivery sheath 72 is disposed in an ascending aorta 84 for deployment of the prosthetic aortic valve, or
- a sheath-introducer electrode, disposed on an introducer used to introduce the sheath into the vasculature at the vascular access site (e.g., the femoral vascular access site); typically, the sheath-introducer electrode is disposed along the introducer.

For some applications, delivery-system control circuitry 80 is configured to drive cathode 130 to apply unipolar rapid ventricular pacing, using anode 136 as the return electrode. Such pacing may temporarily reduce left ventricular output, in order to enable more accurate placement of the prosthetic aortic valve. Delivery-system control circuitry 80 sets the parameters of the pacing signal.

As shown in FIGS. 6C-D, prosthetic aortic valve 120 is also configured to assume an expanded fully-deployed configuration upon being fully released from distal end 82 of delivery sheath 72.

For some applications, as shown in FIG. 6D, valve prosthesis system 68 further comprises an external unit 100. External unit 100 is configured to be disposed outside a body of the patient and comprises (a) energy-transmission coil 102, and (b) external-unit control circuitry 104, which is configured to drive energy-transmission coil 102 to wirelessly transfer energy, by inductive coupling, to prosthetic-valve coil 36 when prosthetic aortic valve 20 is in the expanded fully-deployed configuration, as shown in FIG. 6D. In these applications, after prosthetic aortic valve 20 is fully released from distal end 82 of delivery sheath 72, external-unit control circuitry 104 is activated to drive energy-transmission coil 102 to wirelessly transfer energy, by inductive coupling, to prosthetic-valve coil 36 when prosthetic aortic valve 20 is in the expanded fully-deployed configuration.

Alternatively, valve prosthesis system 68 comprises external unit 100, and does not comprise delivery system 70.

Further alternatively, in some applications, a single external unit may be provided that provides the functionality of both delivery system 70 and external unit 100. The single external unit may comprise control circuitry that is configured to provide the functionality of both delivery-system control circuitry 80 of delivery system 70 and external-unit control circuitry 104 of external unit 100. The single external unit may be configured to operate in a delivery mode and a post-delivery mode. A user control may be provided to switch between the two modes of operation, or the control circuitry may be configured to automatically switch between the two modes of operation.

For some applications, energy-transmission coil 102 is configured to be positioned against the patient's chest, typically over a sternum 110. This positioning of energy-transmission coil 102 provides high transmission efficiency, because the respective axes of energy-transmission coil 102 and prosthetic-valve coil 36 are generally aligned, because of the angle β (beta) formed between prosthetic-valve coil 36 and central longitudinal axis 26 of frame 30 described hereinabove with reference to FIGS. 1-2. This high transmission efficiency may allow prosthetic-valve coil 36 and/or energy-transmission coil 102 to include fewer turns of the coil(s) and/or to have smaller diameters. Alternatively or additionally, this high transmission efficiency may allow external unit 100 to use less power to induce the same amount of current in prosthetic-valve coil 36.

For other applications, energy-transmission coil 102 is configured to be positioned around the patient's neck, such as described hereinbelow with reference to FIG. 9C. This positioning of energy-transmission coil 102 provides high transmission efficiency (although perhaps not as high as when against the patient's chest), because the respective axes of energy-transmission coil 102 and prosthetic-valve coil 36 are generally aligned, because of the angle β (beta) formed between prosthetic-valve coil 36 and central longitudinal axis 26 of frame 30 described hereinabove with reference to FIGS. 1-2.

Further alternatively, for some applications, energy-transmission coil 102 is configured to be positioned on the patient's back. In this configuration, prosthetic-valve coil 36 may be angled to face generally posterio-superiorly, rather than generally anterio-superiorly as shown in the figures.

For example, (a) upstream-most point 24A of mechanical coupling between prosthetic-valve coil 36 and frame 30 and (b) centroid 28 of cathode 54 may be rotationally aligned with each other or rotationally offset from each other about central longitudinal axis 26 by less than 50 degrees, such as less than 30 degrees. This positioning of energy-transmission coil 102 provides high transmission efficiency (although perhaps not as high as when against the patient's chest), because the respective axes of energy-transmission coil 102 and prosthetic-valve coil 36 are generally aligned, because of the angle β (beta) formed between prosthetic-valve coil 36 and central longitudinal axis 26 of frame 30 described hereinabove with reference to FIGS. 1-2.

For some applications in which valve prosthesis system comprises prosthetic aortic valve 20, described hereinabove with reference to FIGS. 1-4, external-unit control circuitry 104 is configured to drive cathode 54 to apply a cathodic current. For some applications in which valve prosthesis system 68 comprises prosthetic aortic valve 120, described hereinabove with reference to FIG. 5, prosthetic-aortic-valve control circuitry 140 is configured to drive cathode 54 to apply a cathodic current.

For some applications in which valve prosthesis system comprises prosthetic aortic valve 20, described hereinabove with reference to FIGS. 1-4, external-unit control circuitry 104 is configured to drive the one or more electrodes 34 to perform pacing post-implantation, e.g., for several months, by applying a pacing signal, such as a standard, chronic pacing signal. External-unit control circuitry 104 sets the parameters of the pacing signal. Such pacing may employ any standard pacing protocol. Such pacing is typically bipolar. For some applications, the pacing is VVI pacing, which is only applied when a QRS complex is not sensed in the ventricle.

For some applications in which valve prosthesis system comprises prosthetic aortic valve 120, described hereinabove with reference to FIG. 5, prosthetic-aortic-valve control circuitry 140 is configured to use the energy received from external-unit control circuitry 104 to drive the one or more electrodes 34 to perform the post-implantation pacing. Alternatively, for some applications in which valve prosthesis system 68 comprises prosthetic aortic valve 120, described hereinabove with reference to FIG. 5, prosthetic-aortic-valve control circuitry 140 is configured to (a) use the one or more electrodes 34 to sense a cardiac signal, and (b) drive prosthetic-valve coil 36 to transmit a wireless signal indicative of the sensed cardiac signal. For some applications, the cardiac sensing is performed using techniques described in U.S. Pat. No. 9,005,106 to Gross et al., which is incorporated herein by reference. In these applications, the one or more electrodes 34 are typically not used to apply pacing, any thus need not be configured as a cathode and an anode. Such sensing may enable early discharge of the patient from the hospital after implantation of prosthetic aortic valve 20, before the possible development of left bundle branch block (LBBB). If LBBB develops, as it does in approximately 20-30% of patients, the LBBB is detected by the sensing, an alert is generated, and the LBBB may be treated as appropriate.

For some applications in which valve prosthesis system comprises prosthetic aortic valve 20, described hereinabove with reference to FIGS. 1-4, external-unit control circuitry 104 (FIG. 6D)) is configured to drive cathode 54 and anode 57 to set parameters of the pacing signal. For example, external-unit control circuitry 104 may be configured to set an amplitude of the pacing signal by modulating an amplitude of the energy wirelessly transferred from the energy-transmission coil to prosthetic-valve coil 36. Alternatively or additionally, for example, external-unit control circuitry 104 may be configured to drive cathode 54 and anode 57 to (a) begin application of each pulse of the pacing signal by beginning wirelessly transferring energy from the energy-transmission coil to prosthetic-valve coil 36, and (b) conclude the application of each pulse of the pacing signal by ceasing wirelessly transferring energy from the energy-transmission coil to prosthetic-valve coil 36.

The inventor has determined that, in some configurations, it is difficult to assess suitable pacing parameters, e.g., due to patient size or patient body mass distribution, or for example due to technical issues such as variable electrical impedance between heart tissue and cathode 54 and anode 57, or the variable relative orientation of energy-transmission coil 102 and prosthetic-valve coil 36. For some applications, therefore, external unit 100 further comprises at least two sensing skin ECG electrodes 106, placed on the patient's skin 108, e.g., on the chest as shown in FIG. 6D. External-unit control circuitry 104 drives cathode 54 and anode 57 to apply a pacing signal to the patient's heart, and to detect at least one cardiac parameter using sensing skin ECG electrodes 106. External-unit control circuitry 104, at least partially responsively to the detected cardiac parameter, sets parameters of the pacing signal, by wirelessly transferring energy from energy-transmission coil 102 to prosthetic-valve coil 36 by inductive coupling. Because prosthetic aortic valve 20 typically does not comprise any active electronic components, the wireless transfer of energy from the energy-transmission coil to prosthetic-valve coil 36 by inductive coupling itself inductively drives the pacing current through prosthetic-valve coil 36.

Alternatively, external unit 100 comprises another type of cardiac sensor, instead of sensing skin ECG electrodes 106. For example, the cardiac sensor may comprise a heart rate sensor, such as an optical heart rate sensor (e.g., which uses photoplethysmography), or an ECG sensor, such as an optical ECG sensor (e.g., a single channel ECG sensor, such as the Si1172 or Si1173 biometric modules, manufactured by Silicon Laboratories Inc., Austin, Tex., USA).

External-unit control circuitry 104 typically analyzes the detected cardiac parameter to assess a level of responsiveness of the heart to the pacing signal. Upon ascertaining that the level of responsiveness is unsatisfactory, external-unit control circuitry 104 increases the strength of the pacing signal responsively to the detected cardiac parameter (e.g., by increasing the amplitude or the duration of the pacing signal). For example, the pulse width (typically 0.1-1 ms, e.g., 0.25-0.8 ms) of pulses of the pacing signal, or current amplitude in the energy-transmission coil may be iteratively increased, until a determination is made that the heart is suitably responding to the pacing pulses applied to the tissue. At this point, optionally, the strength of the pacing signal is further increased, e.g., by 50-150%, for example by 100%.

For some applications, the detected cardiac parameter is a timing feature of cardiac activity (e.g., heart rate, or the timing of a particular feature of the cardiac cycle). In this case, the parameters of the pacing signal may include a timing parameter of the pacing signal, and external-unit control circuitry 104 sets the timing parameter of the pacing signal responsively to the timing feature of the detected cardiac parameter.

It is noted that, as appropriate for a given patient, pacing of the heart may be applied in a manner that is synchronized to the cardiac cycle of the patient (based on the signals received by sensing skin ECG electrodes 106 or the other cardiac sensor), or the pacing may not be synchronized with the cardiac cycle of the patient.

Sensing skin ECG electrodes 106 are typically suction ECG electrodes or configured to be electrically coupled to the skin by an adhesive. In general, conventional ECG electrodes are suitable to be used for sensing skin ECG electrodes 106. It is noted that although conventional ECG electrodes may be used, complete ECG analysis as is known in the field of electrocardiography typically is not performed in order to implement the functions of external-unit control circuitry 104 described hereinabove.

For some applications, energy-transmission coil 102 and/or ECG electrodes 106 (or another cardiac sensor) are incorporated into shirt 300 configured to be worn by the patient (such as embedded into the shirt, or attached to an inner surface of the shirt), such as described hereinbelow with reference to FIGS. 9A-B, and/or incorporated into a band configured to be worn around the patient's chest or as a necklace 400 configured to be worn around the patient's neck, such as described hereinbelow with reference to FIG. 9C. Alternatively or additionally, for some applications, external unit 100 is incorporated into a belt or strap configured to be worn around the patient's chest.

Figure 7:
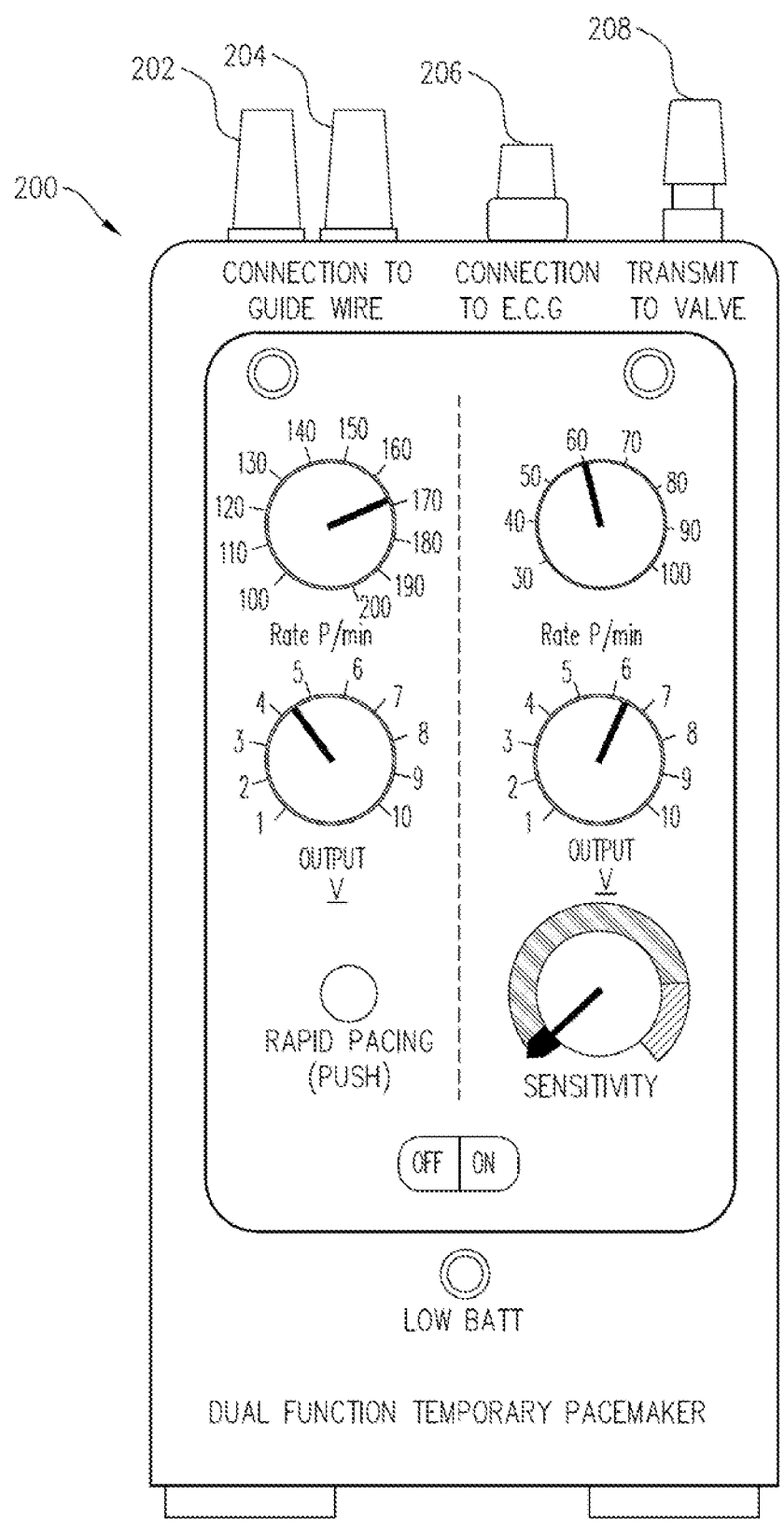
FIG. 7 is a schematic illustration of an external control unit, in accordance with an application of the present invention.

Reference is now made to FIG. 7, which is a schematic illustration of an external control unit 200, in accordance with an application of the present invention. For some applications, external control unit 200 may be configured to provide user-selectable dual-mode pacing, including rapid ventricular pacing for application during an implantation procedure, as described hereinabove with reference to FIGS. 6A-B, and post-implantation chronic bipolar pacing, such as described hereinabove with reference to FIG. 6D. External control unit 200 typically comprises delivery-system control circuitry 80, described hereinabove with reference to FIGS. 6A-B, and external-unit control circuitry 104. As such, external control unit 200 serves the dual role of both a component of delivery system 70, described hereinabove with reference to FIGS. 6A-C, and external unit 100, described hereinabove with reference to FIG. 6.

External control unit 200 typically includes several electrical connectors, to which connection may be made, for example, using connector clips, as known in the art:
an anode connector 202, for connection to anode 136 of delivery system 70;
a cathode connector 204, for connection to cathode 130 of delivery system 70;
an ECG connector 206, for connection to sensing skin ECG electrodes 106; and
a coil connector 208, for connection to energy-transmission coil 102.

Figure 8:
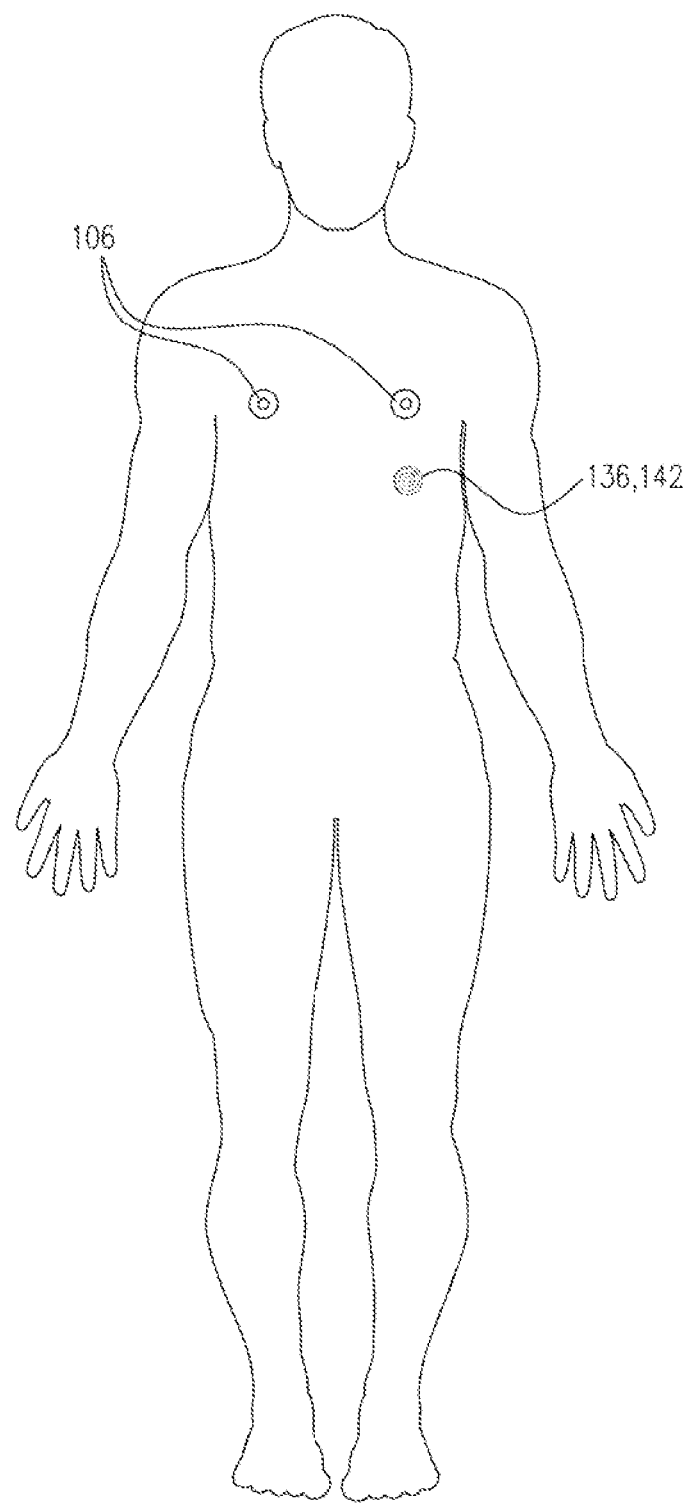
FIG. 8 is a schematic diagram of a patient showing exemplary locations of skin electrodes, in accordance with an application of the present invention.

Reference is now made to FIG. 8, which is a schematic diagram of a patient showing exemplary locations of skin electrodes, in accordance with an application of the present invention. FIG. 8 shows exemplary locations of sensing skin ECG electrodes 106, described hereinabove with reference to FIG. 6D, and anode skin electrode 142, described hereinabove with reference to FIGS. 6A-B.

Figure 9A:
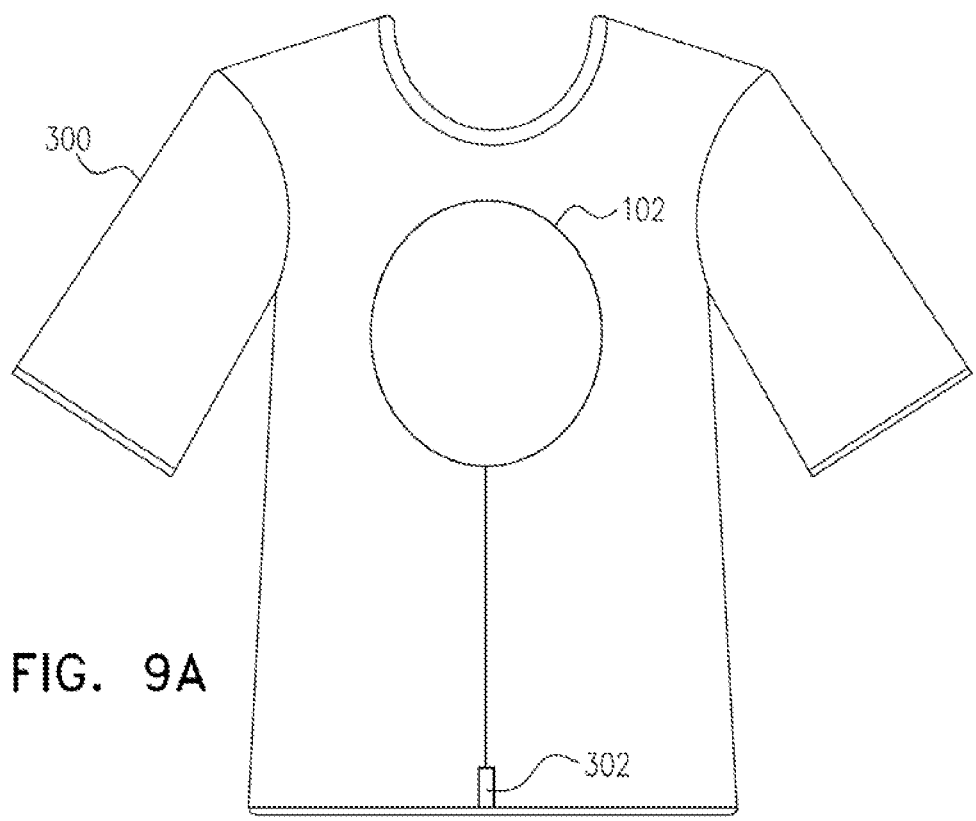
FIGS. 9A-B are schematic illustrations of a shirt with integrated components, in accordance with an application of the present invention.
Figure 9B:
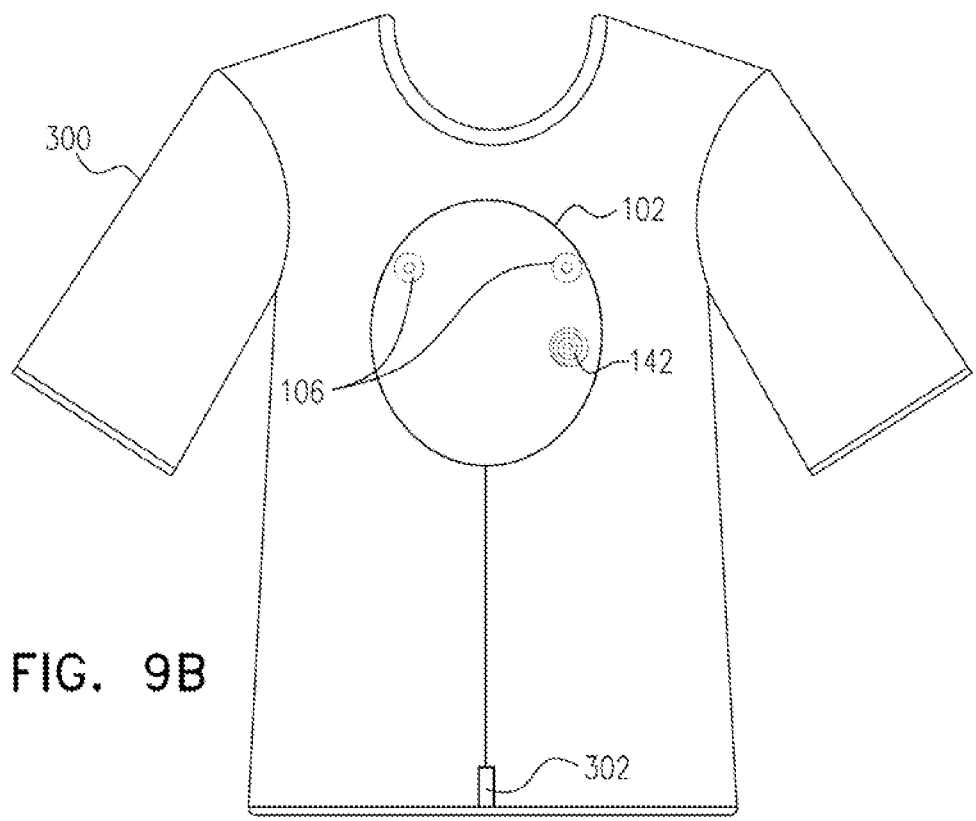

Reference is now made to FIGS. 9A-B, which are schematic illustrations of a shirt 300 with integrated components, in accordance with an application of the present invention. The components may be attached to a surface of the shirt, such as an inner surface, or embedded in the shirt. The components may include:
transmission coil 102, described hereinabove with reference to FIG. 6D;
sensing skin ECG electrodes 106, described hereinabove with reference to FIG. 6D; and/or
anode skin electrode 142, described hereinabove with reference to FIGS. 6A-B.

Typically, shirt 300 further comprises a connector 302, for electrical connection to external control unit 200, described hereinabove with reference to FIG. 7.

Figure 9C:
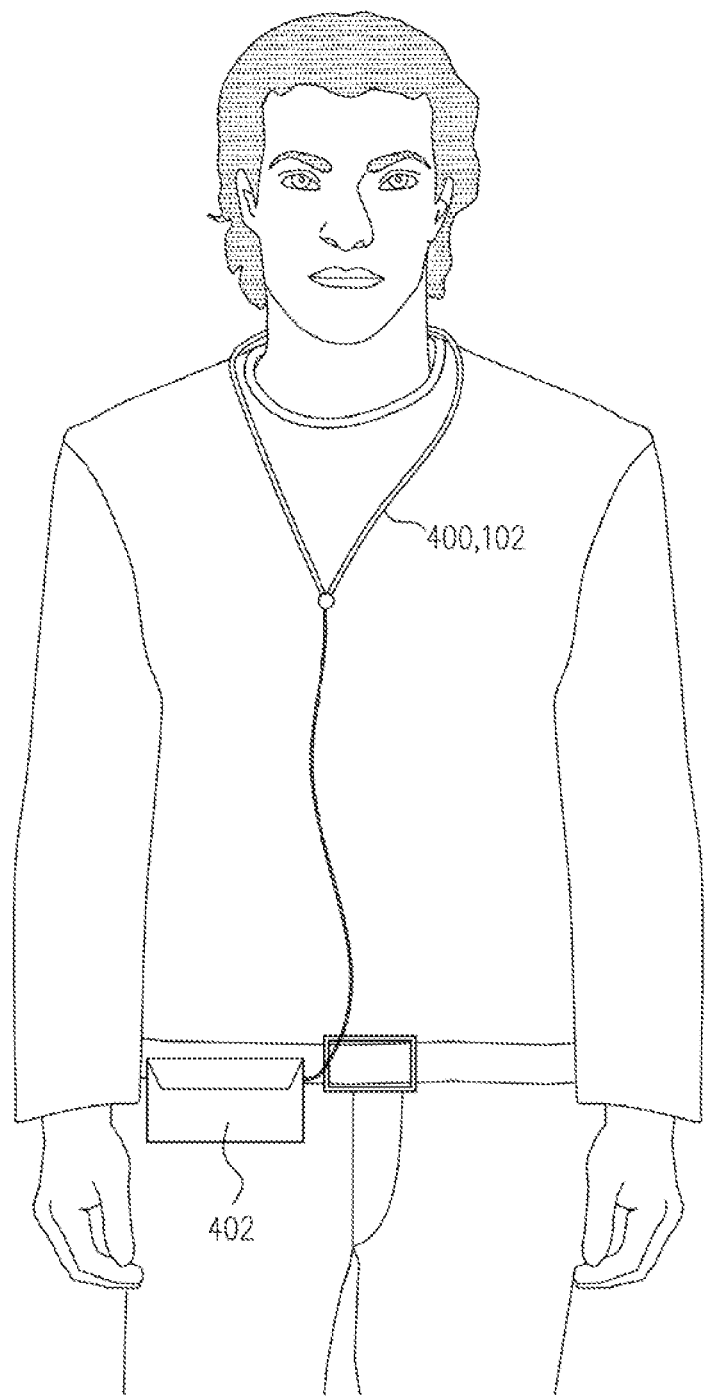
FIG. 9C is a schematic illustration of a necklace, in accordance with an application of the present invention.

Reference is now made to FIG. 9C, which is a schematic illustration of a necklace 400, in accordance with an application of the present invention. As described hereinabove with reference to FIG. 6B, necklace 400 comprises an integrated energy-transmission coil 102.

Alternatively, energy-transmission coil 102 may be integrated into a shirt around the collar, for placement around the patient's neck.

A temporary pacemaker 402 may also be provided.

In an embodiment, techniques and apparatus described in one or more of the following patents and/or applications, which are assigned to the assignee of the present application and are incorporated herein by reference, are combined with techniques and apparatus described herein:
U.S. Pat. No. 10,543,083 to Gross
European Patent Application Publication EP 3508113 A1 to Gross
U.S. Pat. No. 10,835,750 to Gross
US Patent Application Publication 2020/0261224 to Gross
two International Patent Applications to Gross, both filed on even date herewith, both entitled, "Prosthetic Aortic Valve Pacing Systems"

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A prosthetic aortic valve, which is configured to be delivered to a native aortic valve of a patient in a constrained delivery configuration within a delivery sheath, and which comprises:
a frame;
a plurality of prosthetic leaflets coupled to the frame;
a cathode and an anode, which are mechanically coupled to the frame; and
a prosthetic-valve coil, which is coupled to the frame and is in non-wireless electrical communication with the cathode and the anode,
wherein when the prosthetic aortic valve is in an expanded fully-deployed configuration upon release from the delivery sheath, (a) a line defined between upstream-most and downstream-most points of mechanical coupling between the prosthetic-valve coil and the frame and (b) a central longitudinal axis defined by the frame form an angle of between 20 and 70 degrees.

2. The prosthetic aortic valve according to claim 1, wherein the angle is between 30 and 60 degrees.

3. The prosthetic aortic valve according to claim 1, wherein respective non-electrically-insulated end portions of the prosthetic-valve coil define the cathode and the anode.

4. The prosthetic aortic valve according to claim 1, wherein the prosthetic aortic valve does not comprise any active electronic components.

5. The prosthetic aortic valve according to claim 1, wherein when the prosthetic aortic valve is in the expanded fully-deployed configuration, the central longitudinal axis passes through a space surrounded by the prosthetic-valve coil.

6. The prosthetic aortic valve according to claim 1, wherein when the prosthetic aortic valve is in the expanded fully-deployed configuration, (a) a downstream-most point of mechanical coupling between the prosthetic-valve coil and the frame and (b) a centroid of the cathode are rotationally aligned with each other or rotationally offset from each other about the central longitudinal axis by less than 50 degrees.

7. The prosthetic aortic valve according to claim 1, wherein the cathode is located upstream of the anode along the frame.

8. The prosthetic aortic valve according to claim 1, wherein when the prosthetic aortic valve is in the expanded fully-deployed configuration, the frame is shaped so as to define:
   (a) an upstream inflow portion,
   (b) a downstream outflow portion, and
   (c) a constriction portion, which is axially between the upstream inflow portion and the downstream outflow portion, wherein the prosthetic leaflets are coupled to the constriction portion, and wherein when the prosthetic aortic valve is in the expanded fully-deployed configuration, free edges of the prosthetic leaflets face toward the downstream outflow portion, and
   wherein the cathode is coupled to the upstream inflow portion of the frame.

9. The prosthetic aortic valve according to claim 1, wherein when the prosthetic aortic valve is in the expanded fully-deployed configuration, the frame is shaped so as to define:
   (a) an upstream inflow portion,
   (b) a downstream outflow portion, and
   (c) a constriction portion, which is axially between the upstream inflow portion and the downstream outflow portion, wherein the prosthetic leaflets are coupled to the constriction portion, and wherein when the prosthetic aortic valve is in the expanded fully-deployed configuration, (A) free edges of the prosthetic leaflets face toward the downstream outflow portion, and (B) a ring-shaped longitudinal border between the downstream outflow portion and the constriction portion is defined by a downstream-most point of the frame to which the prosthetic leaflets are coupled, and
   wherein a downstream-most point of mechanical coupling between the prosthetic-valve coil and the frame is located on the downstream outflow portion when the prosthetic aortic valve is in the expanded fully-deployed configuration.

10. The apparatus according to claim 9, wherein an upstream-most point of mechanical coupling between the prosthetic-valve coil and the frame is located on the constriction portion when the prosthetic aortic valve is in the expanded fully-deployed configuration.

11. A valve prosthesis system comprising the prosthetic aortic valve according to claim 1, the valve prosthesis system further comprising an external unit, which is configured to be disposed outside a body of the patient, and which comprises:
   an energy-transmission coil; and
   external-unit control circuitry, which is configured to drive the energy-transmission coil to wirelessly transfer energy to the prosthetic-valve coil by inductive coupling.

12. The valve prosthesis system according to claim 11, wherein the external-unit control circuitry is configured to drive the cathode and the anode to apply a pacing signal to a heart of the patient, by wirelessly transferring the energy from the energy-transmission coil to the prosthetic-valve coil by inductive coupling.

13. The valve prosthesis system according to claim 12, wherein the external unit further comprises a cardiac sensor, and
   wherein the external-unit control circuitry is configured to:
      detect at least one cardiac parameter using the cardiac sensor, and
      at least partially responsively to the detected at least one cardiac parameter, set parameters of the pacing signal, by wirelessly transferring the energy from the energy-transmission coil to the prosthetic-valve coil by inductive coupling.

14. The valve prosthesis system according to claim 13, wherein the cardiac sensor comprises at least two sensing skin ECG electrodes.

15. The valve prosthesis system according to claim 11, wherein the external-unit control circuitry is configured to
   wirelessly transfer the energy by generating a plurality of AC pulses, each including a train of AC bursts, and
   wherein the prosthetic aortic valve comprises a passive diode, which is coupled in electrical communication with the prosthetic-valve coil, and is configured to rectify current in the prosthetic-valve coil.

16. The valve prosthesis system according to claim 15, wherein the external-unit control circuitry is configured to generate the train of AC bursts at a frequency of between 3 kHz and 130 kHz.

17. The valve prosthesis system according to claim 15, wherein the external-unit control circuitry is configured to include 20-100 AC bursts in each of the AC pulses.

18. A method comprising:
   delivering, to a native aortic valve of a patient, via vasculature of the patient, a prosthetic aortic valve while in a constrained delivery configuration within a delivery sheath, the prosthetic aortic valve including (a) a frame, (b) a plurality of prosthetic leaflets coupled to the frame, (c) a cathode and an anode, which are mechanically coupled to the frame, and (d) a prosthetic-valve coil, which is coupled to the frame in non-wireless electrical communication with the cathode and the anode; and
   releasing the prosthetic aortic valve from the delivery sheath, such that the prosthetic aortic valve transitions to an expanded fully-deployed configuration, in which (a) a line defined between upstream-most and downstream-most points of mechanical coupling between the prosthetic-valve coil and the frame and (b) a central longitudinal axis defined by the frame form an angle of between 20 and 70 degrees.

19. The method according to claim 18, wherein releasing the prosthetic aortic valve from the delivery sheath comprises releasing the prosthetic aortic valve from the delivery sheath, such that the prosthetic aortic valve transitions to the expanded fully-deployed configuration, in which the central longitudinal axis passes through a space surrounded by the prosthetic-valve coil.

20. The method according to claim 18, further comprising rotationally orienting the prosthetic aortic valve such that the prosthetic-valve coil faces generally anterio-superiorly toward a sternum of the patient.

21. The method according to claim 20,
wherein when the prosthetic aortic valve is in the expanded fully-deployed configuration, (a) a downstream-most point of mechanical coupling between the prosthetic-valve coil and the frame and (b) a centroid of the cathode are rotationally aligned with each other or rotationally offset from each other about the central longitudinal axis by less than 50 degrees, and wherein rotationally orienting the prosthetic aortic valve comprises aligning the cathode adjacent to cardiac tissue near a bundle of His of the patient, so as to automatically align the prosthetic-valve coil facing generally anterio-superiorly toward a sternum of the patient.

22. The method according to claim 18, further comprising activating external-unit control circuitry of an external unit, disposed outside a body of the patient, to drive an energy-transmission coil of the external unit to wirelessly transfer energy to the prosthetic-valve coil by inductive coupling.

23. The method according to claim 22, further comprising positioning the energy-transmission coil against a chest of the patient, over a sternum of the patient.

24. The method according to claim 22, further comprising positioning the energy-transmission coil around a neck of the patient.

25. The method according to claim 22, wherein activating the external-unit control circuitry comprises activating the external-unit control circuitry to drive the cathode and the anode to apply a pacing signal to a heart of the patient, by wirelessly transferring the energy from the energy-transmission coil to the prosthetic-valve coil by inductive coupling.

26. The method according to claim 25, wherein activating the external-unit control circuitry comprises activating the external-unit control circuitry to:
- detect at least one cardiac parameter using a cardiac sensor, and
- at least partially responsively to the detected at least one cardiac parameter, set parameters of the pacing signal, by wirelessly transferring the energy from the energy-transmission coil to the prosthetic-valve coil by inductive coupling.

27. The method according to claim 26, wherein the cardiac sensor includes at least two sensing skin ECG electrodes placed on skin of the patient.

* * * * *